(12) United States Patent
Brown et al.

(10) Patent No.: US 7,988,720 B2
(45) Date of Patent: Aug. 2, 2011

(54) LONGITUDINALLY FLEXIBLE EXPANDABLE STENT

(75) Inventors: Brian J. Brown, Hanover, MN (US); Michael L. Davis, Shorewood, MN (US); Michael P. Meyer, Richfield, MN (US); Daniel Gregorich, St. Louis Park, MN (US); Paul F. Chouinard, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 401 days.

(21) Appl. No.: 11/781,031

(22) Filed: Jul. 20, 2007

(65) Prior Publication Data

US 2008/0065195 A1    Mar. 13, 2008

Related U.S. Application Data

(63) Continuation-in-part of application No. 11/519,552, filed on Sep. 12, 2006, now abandoned.

(51) Int. Cl.
*A61F 2/16* (2006.01)
(52) U.S. Cl. ...................... 623/1.16; 623/1.15
(58) Field of Classification Search .................. 623/1.16
See application file for complete search history.

(56) References Cited

U.S. PATENT DOCUMENTS

| | | |
|---|---|---|
| 2,836,181 A | 5/1958 | Tapp |
| 3,105,492 A | 10/1963 | Jeckel |
| 3,272,204 A | 9/1966 | Artandi et al. |
| 3,490,975 A | 1/1970 | Lightwood et al. |
| 3,509,883 A | 5/1970 | Dibelius |
| 3,526,228 A | 9/1970 | Lyng |
| 3,562,820 A | 2/1971 | Braun |
| 3,635,215 A | 1/1972 | Shea et al. |
| 3,657,744 A | 4/1972 | Ersek |
| 3,771,526 A | 11/1973 | Rudle |
| 3,868,956 A | 3/1975 | Alfidi et al. |
| 3,993,078 A | 11/1976 | Bergentz et al. |

(Continued)

FOREIGN PATENT DOCUMENTS

DE            19840645         3/2000

(Continued)

OTHER PUBLICATIONS

U.S. Appl. No. 60/844,011 to Broome et al filed Sep. 12, 2006.*

(Continued)

*Primary Examiner* — Paul Prebilic
(74) *Attorney, Agent, or Firm* — Vidas, Arrett & Steinkraus, P.A.

(57) ABSTRACT

In at least one embodiment, a stent comprises a plurality of serpentine bands and a plurality of connector columns. Each serpentine band comprises a plurality of alternating straight band struts and turns. Adjacent serpentine bands are connected across a connector column by a plurality of connector struts. Each connector strut is connected at one end to a turn of one serpentine band and connected at the other end to a turn of another serpentine band. The turns of a serpentine band comprise connected turns that connect to a connector strut and unconnected turns that do not connect to a connector strut. At least one serpentine band comprises a repeating pattern of three band struts and then five band struts extending between connected turns as the serpentine band is traversed. At least one serpentine band comprises a repeating pattern of three band struts and then one band strut extending between connected turns as the serpentine band is traversed.

19 Claims, 14 Drawing Sheets

U.S. PATENT DOCUMENTS

| | | |
|---|---|---|
| 4,078,167 A | 3/1978 | Banas et al. |
| 4,127,761 A | 11/1978 | Pauley et al. |
| 4,130,904 A | 12/1978 | Whalen |
| 4,140,126 A | 2/1979 | Choudhury |
| 4,141,364 A | 2/1979 | Schultze |
| 4,164,045 A | 8/1979 | Bokros et al. |
| 4,214,587 A | 7/1980 | Sakura, Jr. |
| 4,300,244 A | 11/1981 | Bokros |
| 4,313,231 A | 2/1982 | Koyamada |
| 4,319,363 A | 3/1982 | Ketharanathan |
| 4,425,908 A | 1/1984 | Simon |
| 4,441,215 A | 4/1984 | Kaster |
| 4,470,407 A | 9/1984 | Hussein |
| 4,501,264 A | 2/1985 | Rockey |
| 4,503,569 A | 3/1985 | Dotter |
| 4,512,338 A | 4/1985 | Balko et al. |
| 4,535,770 A | 8/1985 | Lemole |
| 4,550,447 A | 11/1985 | Seiler, Jr. et al. |
| 4,553,545 A | 11/1985 | Maass et al. |
| 4,560,374 A | 12/1985 | Hammerslag |
| 4,580,568 A | 4/1986 | Gianturco |
| 4,597,389 A | 7/1986 | Ibrahim et al. |
| 4,647,416 A | 3/1987 | Seiler, Jr. et al. |
| 4,649,922 A | 3/1987 | Wiktor |
| 4,655,771 A | 4/1987 | Wallsten |
| 4,655,776 A | 4/1987 | Lesinski |
| 4,665,906 A | 5/1987 | Jervis ..................... 128/92 YN |
| 4,665,918 A | 5/1987 | Garza et al. |
| 4,681,110 A | 7/1987 | Wiktor |
| 4,693,721 A | 9/1987 | Ducheyne |
| 4,733,665 A | 3/1988 | Palmaz |
| 4,739,762 A | 4/1988 | Palmaz |
| 4,740,207 A | 4/1988 | Kreamer |
| 4,760,849 A | 8/1988 | Kropf |
| 4,762,128 A | 8/1988 | Rosenbluth |
| 4,768,507 A | 9/1988 | Fischell et al. |
| 4,769,029 A | 9/1988 | Patel |
| 4,771,773 A | 9/1988 | Kropf |
| 4,776,337 A | 10/1988 | Palmaz |
| 4,787,899 A | 11/1988 | Lazarus |
| 4,795,458 A | 1/1989 | Regan |
| 4,795,465 A | 1/1989 | Marten |
| 4,800,882 A | 1/1989 | Gianturco |
| 4,820,298 A | 4/1989 | Leveen et al. |
| 4,830,003 A | 5/1989 | Wolff et al. |
| 4,842,575 A | 6/1989 | Hoffman, Jr. et al. |
| 4,848,343 A | 7/1989 | Wallsten et al. |
| 4,851,009 A | 7/1989 | Pinchuk |
| 4,856,516 A | 8/1989 | Hillstead |
| 4,872,874 A | 10/1989 | Taheri |
| 4,877,030 A | 10/1989 | Beck et al. |
| 4,878,906 A | 11/1989 | Lindemann et al. |
| 4,886,062 A | 12/1989 | Wiktor |
| 4,913,141 A | 4/1990 | Hillstead |
| 4,922,905 A | 5/1990 | Strecker |
| 4,950,227 A | 8/1990 | Savin et al. |
| 4,950,258 A | 8/1990 | Kawai et al. |
| 4,994,071 A | 2/1991 | MacGregor |
| 5,015,253 A | 5/1991 | MacGregor |
| 5,019,090 A | 5/1991 | Pinchuk |
| 5,035,706 A | 7/1991 | Gianturco et al. |
| 5,037,392 A | 8/1991 | Hillstead |
| 5,059,211 A | 10/1991 | Stack et al. |
| 5,064,435 A | 11/1991 | Porter |
| 5,071,407 A | 12/1991 | Termin et al. ............... 604/104 |
| 5,089,005 A | 2/1992 | Harada .......................... 606/194 |
| 5,091,205 A | 2/1992 | Fan ................................... 427/2 |
| 5,092,877 A | 3/1992 | Pinchuk |
| 5,102,417 A | 4/1992 | Palmaz |
| 5,104,399 A | 4/1992 | Lazarus |
| 5,104,404 A | 4/1992 | Wolff |
| 5,108,415 A | 4/1992 | Pinchuk et al. |
| 5,108,417 A | 4/1992 | Sawyer |
| 5,122,154 A | 6/1992 | Rhodes |
| 5,133,732 A | 7/1992 | Wiktor |
| 5,135,536 A | 8/1992 | Hillstead |
| 5,139,480 A | 8/1992 | Hickle et al. |
| 5,147,385 A | 9/1992 | Beck et al. |
| 5,147,400 A | 9/1992 | Kaplan et al. |
| 5,158,548 A | 10/1992 | Lau et al. |
| 5,163,952 A | 11/1992 | Froix |
| 5,195,984 A | 3/1993 | Schatz |
| 5,197,978 A | 3/1993 | Hess |
| 5,217,483 A | 6/1993 | Tower |
| 5,226,913 A | 7/1993 | Pinchuk |
| 5,282,823 A | 2/1994 | Schwartz et al. |
| 5,282,824 A | 2/1994 | Gianturco |
| 5,292,331 A | 3/1994 | Boneau |
| 5,304,121 A | 4/1994 | Sahatjian ..................... 604/509 |
| 5,304,200 A | 4/1994 | Spaulding |
| 5,314,472 A | 5/1994 | Fontaine ........................ 623/12 |
| 5,344,425 A | 9/1994 | Sawyer |
| 5,354,308 A | 10/1994 | Simon et al. |
| 5,354,309 A | 10/1994 | Schnepp-Pesch et al. |
| 5,356,423 A | 10/1994 | Tihon et al. ................. 623/1.15 |
| 5,370,683 A | 12/1994 | Fontaine ........................... 623/1 |
| 5,383,892 A | 1/1995 | Cardon et al. |
| 5,389,106 A | 2/1995 | Tower ........................... 606/198 |
| 5,405,377 A | 4/1995 | Cragg |
| 5,449,373 A | 9/1995 | Pinchasik et al. ............. 606/198 |
| 5,507,767 A | 4/1996 | Maeda et al. .................. 606/198 |
| 5,514,154 A | 5/1996 | Lau et al. |
| 5,527,354 A | 6/1996 | Fontaine et al. ................ 623/12 |
| 5,545,210 A | 8/1996 | Hess et al. ....................... 623/12 |
| 5,549,663 A | 8/1996 | Cottone, Jr. ..................... 623/12 |
| 5,554,181 A | 9/1996 | Das .................................... 623/1 |
| 5,591,197 A | 1/1997 | Orth et al. ..................... 606/198 |
| 5,591,227 A | 1/1997 | Dinh et al. ........................ 623/1 |
| 5,591,230 A | 1/1997 | Horn et al. ....................... 623/1 |
| 5,593,442 A | 1/1997 | Klein ............................... 623/12 |
| 5,599,352 A | 2/1997 | Dinh et al. ........................ 623/1 |
| 5,613,981 A | 3/1997 | Boyle et al. ................... 606/198 |
| 5,624,411 A | 4/1997 | Tuch .............................. 604/265 |
| 5,630,829 A | 5/1997 | Lauterjung ..................... 606/198 |
| 5,643,312 A | 7/1997 | Fischell et al. ................. 606/198 |
| 5,653,727 A | 8/1997 | Wiktor ........................... 606/195 |
| 5,674,241 A | 10/1997 | Bley et al. ..................... 606/198 |
| 5,679,400 A | 10/1997 | Tuch .............................. 427/2.14 |
| 5,683,450 A | 11/1997 | Boicoechea et al. .............. 623/1 |
| 5,697,971 A | 12/1997 | Fischell et al. ................ 606/192 |
| 5,700,285 A | 12/1997 | Myers et al. ...................... 623/1 |
| 5,707,386 A | 1/1998 | Schnepp-Pesch et al. |
| 5,716,365 A | 2/1998 | Goicoechea et al. ........... 606/108 |
| 5,716,393 A | 2/1998 | Lindenberg et al. .............. 623/1 |
| 5,718,724 A | 2/1998 | Goicoechea et al. .............. 623/1 |
| 5,725,572 A | 3/1998 | Lam et al. ..................... 623/1.16 |
| 5,728,158 A | 3/1998 | Lau et al. ..................... 623/23.7 |
| 5,733,303 A | 3/1998 | Israel et al. .................... 606/198 |
| 5,735,871 A | 4/1998 | Sgro ............................. 606/198 |
| 5,735,892 A | 4/1998 | Meyers et al. .................... 623/1 |
| 5,735,893 A | 4/1998 | Lau et al. ......................... 623/1 |
| 5,741,333 A | 4/1998 | Frid ................................. 623/12 |
| 5,749,880 A | 5/1998 | Banas et al. ................... 606/198 |
| 5,755,770 A | 5/1998 | Ravenscroft ...................... 623/1 |
| 5,755,781 A | 5/1998 | Jayaraman .................... 623/1.16 |
| 5,759,192 A | 6/1998 | Saunders ....................... 606/194 |
| 5,776,161 A | 7/1998 | Globerman ................... 606/194 |
| 5,776,180 A | 7/1998 | Goicoechea et al. .............. 623/1 |
| 5,776,183 A | 7/1998 | Kanesaka et al. .............. 606/194 |
| 5,800,508 A | 9/1998 | Goicoechea et al. .............. 623/1 |
| 5,800,514 A | 9/1998 | Nunez et al. ................. 623/1.51 |
| 5,800,521 A | 9/1998 | Orth ............................... 606/195 |
| 5,800,524 A | 9/1998 | Borghi .............................. 623/1 |
| 5,807,404 A | 9/1998 | Richter ............................. 623/1 |
| 5,810,872 A | 9/1998 | Kanesaka et al. .............. 606/198 |
| 5,817,404 A | 10/1998 | Kawakita et al. .............. 428/209 |
| 5,824,043 A | 10/1998 | Cottone, Jr. ....................... 623/1 |
| 5,824,045 A | 10/1998 | Alt .................................... 623/1 |
| 5,824,046 A | 10/1998 | Smith et al. ....................... 623/1 |
| 5,824,048 A | 10/1998 | Tuch ................................. 623/1 |
| 5,824,059 A | 10/1998 | Wijay ........................... 623/1.15 |
| 5,827,321 A * | 10/1998 | Roubin et al. ................ 623/1.16 |
| 5,836,966 A | 11/1998 | St. Germain .................. 606/198 |
| 5,843,117 A | 12/1998 | Alt et al. ........................ 606/194 |
| 5,843,158 A | 12/1998 | Lenker et al. ..................... 623/1 |
| 5,855,600 A | 1/1999 | Alt ................................. 606/195 |
| 5,860,999 A | 1/1999 | Schnepp-Pesch et al. .... 606/194 |

| | | | |
|---|---|---|---|
| 5,868,782 A | 2/1999 | Frantzen .................. 606/198 |
| 5,876,432 A | 3/1999 | Lau et al. ........................ 623/1 |
| 5,876,449 A | 3/1999 | Starck et al. ................ 623/23.7 |
| 5,895,406 A | 4/1999 | Gray et al. ................. 606/198 |
| 5,897,588 A | 4/1999 | Hull et al. ........................ 623/1 |
| 5,897,589 A | 4/1999 | Cottenceau ..................... 623/1 |
| 5,900,246 A | 5/1999 | Lambert ....................... 424/429 |
| 5,902,317 A | 5/1999 | Kleshinski et al. ........... 606/198 |
| 5,902,332 A | 5/1999 | Schatz ............................ 623/1 |
| 5,911,732 A | 6/1999 | Hojeibane .................... 606/194 |
| 5,911,754 A | 6/1999 | Kanesaka et al. .................. 623/1 |
| 5,913,895 A | 6/1999 | Burpee et al. .................. 623/1 |
| 5,913,897 A | 6/1999 | Corso, Jr. et al. .............. 623/1 |
| 5,916,263 A | 6/1999 | Goicoechea et al. ............. 623/1 |
| 5,922,021 A | 7/1999 | Jang ................................ 623/1 |
| 5,925,061 A | 7/1999 | Ogi et al. ...................... 606/198 |
| 5,928,279 A | 7/1999 | Shannon et al. ................. 623/1 |
| 5,935,161 A | 8/1999 | Robinson et al. ................ 623/1 |
| 5,935,162 A | 8/1999 | Dang .............................. 623/1 |
| 5,938,682 A | 8/1999 | Hojeibane et al. ............. 606/198 |
| 5,938,696 A | 8/1999 | Goicoechea et al. ............. 623/1 |
| 5,938,697 A * | 8/1999 | Killion et al. ................ 623/1.15 |
| 5,948,016 A | 9/1999 | Jang ................................ 623/1 |
| 5,951,586 A | 9/1999 | Berg et al. .................... 606/198 |
| 5,954,743 A | 9/1999 | Jang ........................... 623/1.15 |
| 5,957,930 A | 9/1999 | Vrba ............................. 606/108 |
| 5,961,545 A | 10/1999 | Lentz ................................ 623/1 |
| 5,964,798 A | 10/1999 | Imran ................................ 623/1 |
| 5,972,018 A | 10/1999 | Israel et al. ................. 623/1.15 |
| 5,980,553 A | 11/1999 | Gray et al. .................... 606/198 |
| 5,984,016 A | 11/1999 | Samuelsson ................... 169/62 |
| 6,001,125 A | 12/1999 | Golds et al. ..................... 623/1 |
| 6,013,854 A | 1/2000 | Moriuchi ....................... 606/194 |
| 6,017,363 A | 1/2000 | Hojeibane ......................... 623/1 |
| 6,017,365 A | 1/2000 | Von Oepen ........................ 623/1 |
| 6,027,526 A | 2/2000 | Limon et al. ................. 623/1.15 |
| 6,033,433 A | 3/2000 | Ehr et al. .......................... 623/1 |
| 6,039,756 A | 3/2000 | Jang ........................... 623/1.15 |
| 6,042,597 A | 3/2000 | Kveen et al. .................. 606/198 |
| 6,051,020 A | 4/2000 | Goicoechea et al. ............. 623/1 |
| 6,053,940 A | 4/2000 | Wijay ............................... 623/1 |
| 6,068,656 A | 5/2000 | Von Oepen ................. 623/1.17 |
| 6,083,259 A | 7/2000 | Frantzen ..................... 623/1.15 |
| 6,090,127 A | 7/2000 | Globerman .................... 606/194 |
| 6,106,548 A | 8/2000 | Roubin et al. ................. 623/1.15 |
| 6,113,627 A | 9/2000 | Jang ................................ 623/1 |
| 6,117,165 A | 9/2000 | Becker ............................ 623/1 |
| 6,120,522 A | 9/2000 | Vrba et al. ................... 606/190 |
| 6,123,712 A | 9/2000 | Di Caprio et al. ............. 606/108 |
| 6,123,721 A | 9/2000 | Jang ................................ 623/1 |
| 6,124,523 A | 9/2000 | Banas et al. ..................... 623/11 |
| 6,129,755 A | 10/2000 | Mathis et al. ............... 623/1.15 |
| 6,132,460 A | 10/2000 | Thompson ....................... 623/1 |
| 6,132,461 A | 10/2000 | Thompson .................. 623/1.15 |
| 6,133,627 A | 10/2000 | Khandros et al. ............. 257/692 |
| 6,139,573 A | 10/2000 | Sogard et al. ............... 623/1.13 |
| 6,152,957 A | 11/2000 | Jang ........................... 623/1.37 |
| 6,156,052 A | 12/2000 | Richter et al. ................. 606/191 |
| 6,159,237 A | 12/2000 | Alt et al. .................... 623/1.11 |
| 6,159,238 A | 12/2000 | Killion et al. ............... 623/1.11 |
| 6,162,243 A | 12/2000 | Gray et al. .................. 623/1.11 |
| 6,179,867 B1 | 1/2001 | Cox ............................ 623/1.15 |
| 6,187,034 B1 | 2/2001 | Frantzen ..................... 623/1.11 |
| 6,190,403 B1 | 2/2001 | Fischell et al. .................... 623/1 |
| 6,193,744 B1 | 2/2001 | Ehr et al. .......................... 623/1 |
| 6,193,747 B1 | 2/2001 | Von Oepen ................. 623/1.15 |
| 6,200,334 B1 | 3/2001 | Jang ............................ 623/1.1 |
| 6,206,911 B1 | 3/2001 | Milo ............................ 623/1.15 |
| 6,217,608 B1 | 4/2001 | Penn et al. .................. 623/1.16 |
| 6,231,598 B1 | 5/2001 | Berry et al. ................. 623/1.15 |
| 6,235,053 B1 | 5/2001 | Jang ........................... 623/1.15 |
| 6,238,430 B1 | 5/2001 | Klumb et al. ............... 623/1.15 |
| 6,241,039 B1 | 6/2001 | Jarnstrom et al. .......... 180/69.21 |
| 6,241,760 B1 | 6/2001 | Jang ........................... 623/1.12 |
| 6,261,319 B1 | 7/2001 | Kveen et al. ................ 623/1.15 |
| 6,273,910 B1 | 8/2001 | Limon ........................ 623/1.15 |
| 6,273,911 B1 | 8/2001 | Cox et al. ................... 623/1.15 |
| 6,331,189 B1 | 12/2001 | Wolinsky et al. ........... 623/1.15 |
| 6,342,067 B1 | 1/2002 | Mathis et al. ............... 623/1.15 |
| 6,348,065 B1 * | 2/2002 | Brown et al. ................ 623/1.16 |
| 6,355,059 B1 | 3/2002 | Richter et al. ............... 623/1.17 |
| 6,355,063 B1 | 3/2002 | Calcote ....................... 623/1.42 |
| 6,358,274 B1 | 3/2002 | Thompson ................... 623/1.15 |
| 6,361,759 B1 | 3/2002 | Frayne et al. ............... 424/9.323 |
| 6,364,903 B2 | 4/2002 | Tseng et al. .................. 623/1.15 |
| 6,379,379 B1 | 4/2002 | Wang ......................... 623/1.15 |
| 6,379,382 B1 | 4/2002 | Yang ........................... 623/1.42 |
| 6,383,214 B1 | 5/2002 | Banas et al. .................. 623/1.14 |
| 6,387,122 B1 | 5/2002 | Cragg ........................... 623/1.16 |
| 6,395,212 B1 | 5/2002 | Solem ......................... 264/230 |
| 6,398,803 B1 | 6/2002 | Layne et al. ................. 623/1.13 |
| 6,409,753 B1 | 6/2002 | Brown et al. ................ 623/1.15 |
| 6,409,761 B1 | 6/2002 | Jang ............................ 623/6.12 |
| 6,416,538 B1 | 7/2002 | Ley et al. |
| 6,416,543 B1 | 7/2002 | Hilaire et al. |
| 6,423,090 B1 | 7/2002 | Hancock |
| 6,432,133 B1 | 8/2002 | Lau et al. |
| 6,443,982 B1 | 9/2002 | Israel et al. |
| 6,451,047 B2 | 9/2002 | McCrea et al. |
| 6,451,049 B2 | 9/2002 | Vallana et al. |
| 6,451,052 B1 | 9/2002 | Burmeister et al. |
| 6,461,380 B1 | 10/2002 | Cox |
| 6,461,381 B2 | 10/2002 | Israel et al. |
| 6,464,720 B2 | 10/2002 | Boatman et al. |
| 6,464,722 B2 | 10/2002 | Israel et al. |
| 6,468,302 B2 | 10/2002 | Cox et al. |
| 6,471,720 B1 | 10/2002 | Ehr et al. |
| 6,475,233 B2 | 11/2002 | Trozera |
| 6,475,235 B1 | 11/2002 | Jayaraman |
| 6,475,236 B1 | 11/2002 | Roubin et al. |
| 6,478,816 B1 | 11/2002 | Kveen et al. |
| 6,485,508 B1 | 11/2002 | McGuinness |
| 6,485,509 B1 | 11/2002 | Killion et al. |
| 6,488,700 B2 | 12/2002 | Klumb et al. |
| 6,488,701 B1 | 12/2002 | Nolting et al. |
| 6,503,270 B1 | 1/2003 | Richter et al. |
| 6,506,201 B2 | 1/2003 | DiCaprio et al. |
| 6,506,211 B1 | 1/2003 | Skubitz et al. |
| 6,511,505 B2 | 1/2003 | Cox et al. .................... 623/1.16 |
| 6,514,283 B2 | 2/2003 | DiMatteo et al. ............ 623/1.13 |
| 6,520,984 B1 | 2/2003 | Garrison et al. ............. 623/1.11 |
| 6,540,774 B1 | 4/2003 | Cox ............................ 623/1.15 |
| 6,547,814 B2 | 4/2003 | Edwin et al. ................ 623/1.13 |
| 6,547,815 B2 | 4/2003 | Myers ......................... 623/1.13 |
| 6,558,414 B2 | 5/2003 | Layne ......................... 623/1.13 |
| 6,558,415 B2 | 5/2003 | Thompson ................... 623/1.16 |
| 6,569,193 B1 | 5/2003 | Cox et al. .................... 623/1.15 |
| 6,579,314 B1 | 6/2003 | Lombardi et al. ........... 623/1.44 |
| 6,582,461 B1 | 6/2003 | Burmeister et al. .......... 623/1.18 |
| 6,596,022 B2 | 7/2003 | Lau et al. .................... 623/1.16 |
| 6,602,285 B1 | 8/2003 | Von Oepen et al. ......... 623/1.14 |
| 6,730,116 B1 | 5/2004 | Wolinsky et al. ........... 623/1.15 |
| 6,770,088 B1 | 8/2004 | Jang ............................ 623/1.16 |
| 6,776,793 B2 | 8/2004 | Brown et al. ................ 623/1.15 |
| 6,818,014 B2 | 11/2004 | Brown et al. ................ 623/1.16 |
| 6,854,172 B2 | 2/2005 | Kaese et al. ................... 29/412 |
| 6,913,619 B2 | 7/2005 | Brown et al. ................ 623/1.16 |
| 6,962,603 B1 | 11/2005 | Brown et al. ................ 623/1.15 |
| 6,981,986 B1 | 1/2006 | Brown et al. ................ 623/1.16 |
| 7,112,216 B2 | 9/2006 | Gregorich ................... 623/1.15 |
| 7,131,993 B2 | 11/2006 | Gregorich ................... 623/1.16 |
| 7,179,285 B2 | 2/2007 | Ikeuchi et al. ............... 623/1.15 |
| 7,763,011 B2 * | 7/2010 | Ortiz et al. .................. 604/509 |
| 2001/0020183 A1 | 9/2001 | Jang ........................... 623/1.15 |
| 2001/0027339 A1 | 10/2001 | Boatman et al. ............ 623/1.34 |
| 2001/0039446 A1 | 11/2001 | Edwin et al. ................ 623/1.13 |
| 2001/0041929 A1 | 11/2001 | Oepen ......................... 623/1.15 |
| 2001/0041930 A1 | 11/2001 | Globerman et al. ......... 623/1.16 |
| 2001/0044650 A1 | 11/2001 | Simso et al. ................. 623/1.16 |
| 2001/0049551 A1 | 12/2001 | Tseng et al. ................. 623/1.15 |
| 2001/0056298 A1 | 12/2001 | Brown et al. ................ 623/1.16 |
| 2002/0007212 A1 * | 1/2002 | Brown et al. ................ 623/1.16 |
| 2002/0040237 A1 | 4/2002 | Lentz et al. .................. 623/1.13 |
| 2002/0042647 A1 | 4/2002 | Jang ............................ 623/1.15 |
| 2002/0055770 A1 | 5/2002 | Doran et al. ................. 623/1.15 |
| 2002/0091437 A1 | 7/2002 | Tseng et al. .................. 623/1.13 |
| 2002/0095208 A1 | 7/2002 | Gregorich et al. ........... 623/1.15 |
| 2002/0111669 A1 | 8/2002 | Pazienza et al. ............. 623/1.15 |

| | | | |
|---|---|---|---|
| 2002/0120327 A1 | 8/2002 | Cox et al. | 623/1.16 |
| 2002/0177893 A1 | 11/2002 | Brown et al. | 623/1.16 |
| 2003/0014101 A1 | 1/2003 | Harrison | 623/1.15 |
| 2003/0033007 A1 | 2/2003 | Sirhan et al. | 623/1.42 |
| 2003/0069633 A1 | 4/2003 | Richter et al. | 623/1.22 |
| 2003/0074056 A1 | 4/2003 | Killion et al. | 623/1.16 |
| 2003/0144729 A1 | 7/2003 | Bicek et al. | 623/1.16 |
| 2003/0225448 A1* | 12/2003 | Gerberding | 623/1.15 |
| 2004/0024444 A1 | 2/2004 | Moore | 623/1.15 |
| 2004/0093073 A1 | 5/2004 | Lowe et al. | |
| 2004/0167615 A1 | 8/2004 | Lenz | 623/1.16 |
| 2004/0186550 A1* | 9/2004 | Bonsignore | 623/1.15 |
| 2004/0230294 A1 | 11/2004 | Fischell et al. | 623/1.16 |
| 2004/0243216 A1* | 12/2004 | Gregorich | 623/1.15 |
| 2004/0267353 A1 | 12/2004 | Gregorich | 623/1.16 |
| 2005/0015136 A1 | 1/2005 | Ikeuchi et al. | 623/1.15 |
| 2006/0052864 A1 | 3/2006 | Harder et al. | 623/1.38 |
| 2006/0129230 A1 | 6/2006 | Gregorich | 623/1.16 |
| 2007/0100434 A1 | 5/2007 | Gregorich et al. | 623/1.16 |
| 2007/0112419 A1 | 5/2007 | Yadin | 623/1.35 |
| 2007/0225796 A1 | 9/2007 | Yadin et al. | 623/1.16 |

FOREIGN PATENT DOCUMENTS

| | | |
|---|---|---|
| EP | 0 364 787 B1 | 4/1990 |
| EP | 0 540 290 A2 | 5/1993 |
| EP | 0 541 443 A1 | 5/1993 |
| EP | 0 606 165 A1 | 7/1994 |
| EP | 0884029 | 12/1998 |
| EP | 0 938 879 | 2/1999 |
| EP | 1025812 A1 * | 8/2000 |
| EP | 1 245 203 A2 | 10/2002 |
| EP | 1356789 | 10/2003 |
| JP | 6-4175 | 3/1994 |
| WO | 94/17754 | 8/1994 |
| WO | 96/03092 | 2/1996 |
| WO | 97/32543 | 9/1997 |
| WO | 98/40035 | 9/1998 |
| WO | 99/01088 | 1/1999 |
| WO | 99/15107 | 4/1999 |
| WO | 99/38457 | 8/1999 |
| WO | 00/28922 | 5/2000 |
| WO | 00/30563 | 6/2000 |
| WO | 01/01885 | 1/2001 |
| WO | 01/41675 | 6/2001 |
| WO | 02/22024 | 3/2002 |
| WO | 02/055120 | 7/2002 |
| WO | 02/060344 | 8/2002 |
| WO | 03082154 | 10/2003 |

OTHER PUBLICATIONS

U.S. Appl. No. 60/859,460 to Yadin filed Nov. 16, 2006.*
U.S. Appl. No. 11/519,552, filed Sep. 12, 2006, Brown et al.
Starck, E., "First Clinical Experience with the Memotherm Vascular Stent", *STENTS State of the Art Future Developments*, pp. 59-62 (Jun. 1995).
Melzer, A. et al., Performance Improvement of Surgical Instrumentation Through the Use of NI-Ti Materials, *Proceedings of SMST-94 The First International Conference on Shape Memory and Superelastic Technologies*, pp. 401-409 (Mar. 7-10, 1994).
*Manufacturing Processes for Engineering Materials*, by Serope Kalpakjian, Illinois Institute of Technology, Addison-Wesley Publishing Company, pp. 340.
A View of Vascular Stents, by Richard A. Schatz, MD, From the Arizona Heart Institute Foundation, Phoenix, Arizona, *Circulation*, vol. 79, No. 2, Feb. 1989, pp. 445-457.
The Self-Expanding Mesh Stent, by Ulrich Sigwart, Section IV, Chapter 19, pp. 605-610.
Japanese Infringement Search on Articulated Expandable Stents, Dated Jul. 12, 1995.
*Engineering Fluid Mechanics, Third Edition*, John A. Roberson and Clayton T. Crowe, pp. 94 and pp. 414-421.
*Cambridge Dictionary of Science and Technology*, Cambridge University Pressp. 128.
Improved Dilation Catheter Balloons, by Stanley B. Levy, Ph.D., *Journal of Clinical Engineering*, vol. 11, No. 4, Jul.-Aug. 1986, pp. 291-296.
Self-expanding Stainless Steel Biliary Stents, by Harold G. Coons, MD, *Radiology* 1989, vol. 170, No. 3, Part 2, pp. 979-983.
Technical Note Entitled Modifications of Gianturco Expandable Wire Stents, by Barry T. Uchida et al., *AJR*, vol. 150, May 1988, pp. 1185-1187.
Brochure from Cook Incorporated regarding Gianturco-Rosch Biliary Z-StentsTM.
Expandable Biliary Endoprosthesis: An Experimental Study, by Carrasco et al., *AJR*, vol. 145, Dec. 1985, pp. 1279-1282.
Gianturco Expandable Metallic Biliary Stents: Results of a European Clinical Trial, by Irving, et al., *Interventional Radiology*, vol. 172, No. 2, Aug. 1989, pp. 321-326.
Tracheobronchial Tree: Expandable Metallic Stents Used in Experimental and Clinical Applications, Work in Progress, by Wallace et al., *Radiology*, Feb. 1986, pp. 309-312.
Brochure Entitled *Ave Micro STENTtm*, Instructions for Use, by Applied Fascular Engineering, Inc., pp. 1-15.
Brochure Entitled *Micro STENTtm*, by Applied Vascular Engineering, Inc.
"The Jostent Coronary Stent Range," Nicolaus Reifart, "Handbook of Coronary Stents," 2002, pp. 122-125; figure 16.1.

* cited by examiner

LONGITUDINALLY FLEXIBLE EXPANDABLE STENT

CROSS-REFERENCE TO RELATED APPLICATIONS

This Application claims priority to and is a continuation-in-part of U.S. patent application Ser. No. 11/519,552, filed Sep. 12, 2006 (now abandoned), the entire contents of which is hereby incorporated herein by reference.

BACKGROUND OF THE INVENTION

1. Field of the Invention

In some embodiments this invention relates to implantable medical devices, their manufacture, and methods of use.

2. Description of the Related Art

A stent is a medical device introduced to a body lumen and is well known in the art. Typically, a stent is implanted in a blood vessel at the site of a stenosis or aneurysm endoluminally, i.e. by so-called "minimally invasive techniques" in which the stent in a radially reduced configuration, optionally restrained in a radially compressed configuration by a sheath and/or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

Stents, grafts, stent-grafts, vena cava filters, expandable frameworks, and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. Stents may be used to reinforce body vessels and to prevent restenosis following angioplasty in the vascular system. They may be self-expanding, expanded by an internal radial force, such as when mounted on a balloon, or a combination of self-expanding and balloon expandable (hybrid expandable).

Stents may be created by methods including cutting or etching a design from a tubular stock, from a flat sheet which is cut or etched and which is subsequently rolled or from one or more interwoven wires or braids.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In at least one embodiment, a stent comprises a plurality of serpentine bands and a plurality of connector columns. Each serpentine band comprises a plurality of alternating straight band struts and turns. Adjacent serpentine bands are connected across a connector column by a plurality of connector struts. Each connector strut is connected at one end to a turn of one serpentine band and connected at the other end to a turn of another serpentine band. The turns of a serpentine band comprise connected turns that connect to a connector strut and unconnected turns that do not connect to a connector strut. At least one serpentine band comprises a repeating pattern of three band struts and then five band struts extending between connected turns as the serpentine band is traversed. At least one serpentine band comprises a repeating pattern of three band struts and then one band strut extending between connected turns as the serpentine band is traversed.

In at least one embodiment, a stent comprises a plurality of serpentine bands and a plurality of connector columns. Each serpentine band comprises a plurality of alternating straight band struts and turns. Adjacent serpentine bands are connected across a connector column by a plurality of connector struts. Each connector strut is connected at one end to a turn of one serpentine band and connected at the other end to a turn of another serpentine band. The turns of a serpentine band comprise connected turns that connect to a connector strut and unconnected turns that do not connect to a connector strut. At least one serpentine band comprises a repeating pattern of three band struts extending between connected turns as the serpentine band is traversed. At least one serpentine band comprises a repeating pattern of three band struts and then one band strut extending between connected turns as the serpentine band is traversed.

These and other embodiments which characterize the invention are pointed out with particularity in the claims annexed hereto and forming a part hereof. However, for further understanding of the invention, its advantages and objectives obtained by its use, reference should be made to the drawings which form a further part hereof and the accompanying descriptive matter, in which there are illustrated and described further embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

Figure 1:
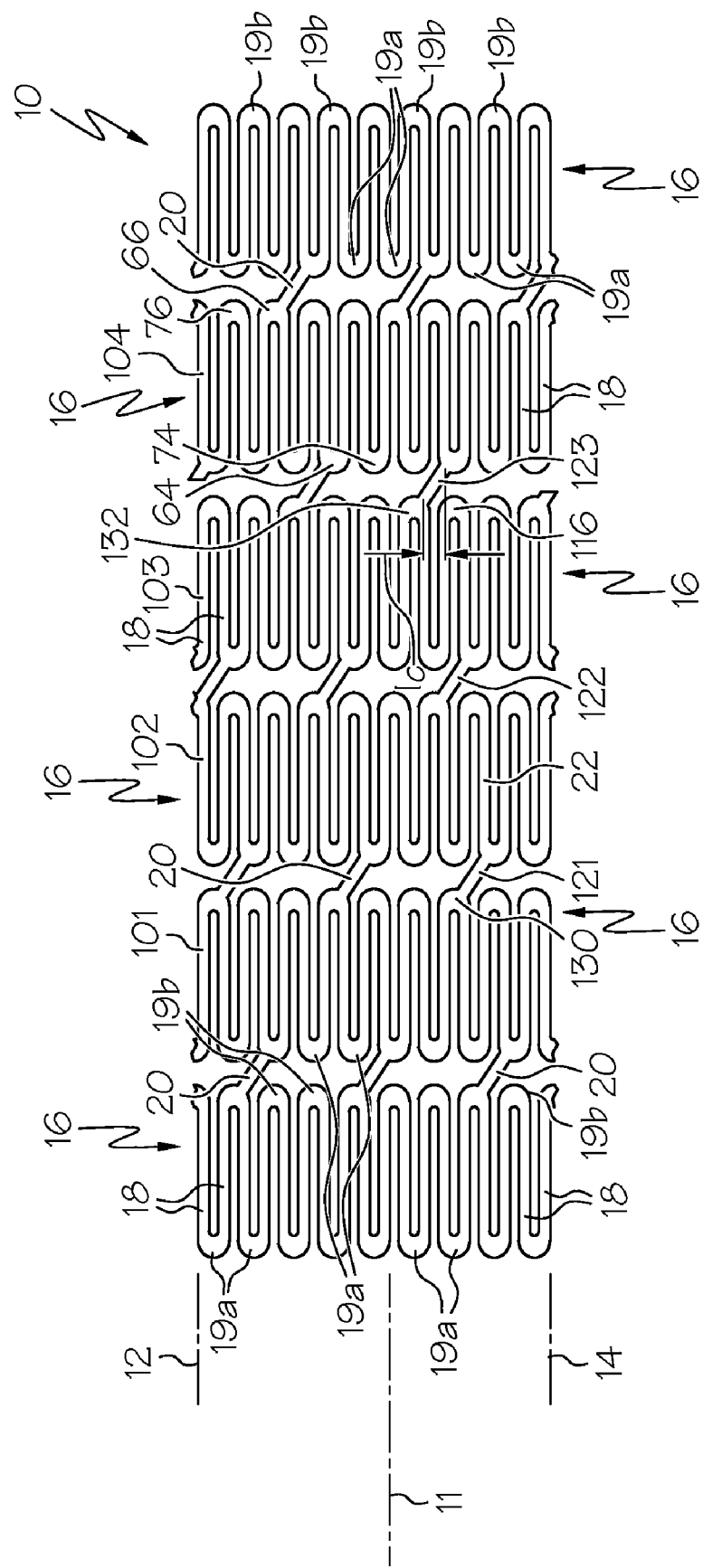
FIG. 1 shows a flat view of an embodiment of an unexpanded stent configuration.

While this invention may be embodied in many different forms, there are described in detail herein specific embodiments of the invention. This description is an exemplification of the principles of the invention and is not intended to limit the invention to the particular embodiments illustrated.

The entire disclosure of US Patent Application Attorney Docket No. S63-13089-US01 is hereby incorporated herein by reference.

The entire disclosures of U.S. patent application Ser. Nos. 11/604,613, 60/859,460 and 60/844,011 are hereby incorporated herein by reference.

For the purposes of this disclosure, like reference numerals in the figures shall refer to like features unless otherwise indicated.

Figure 2:
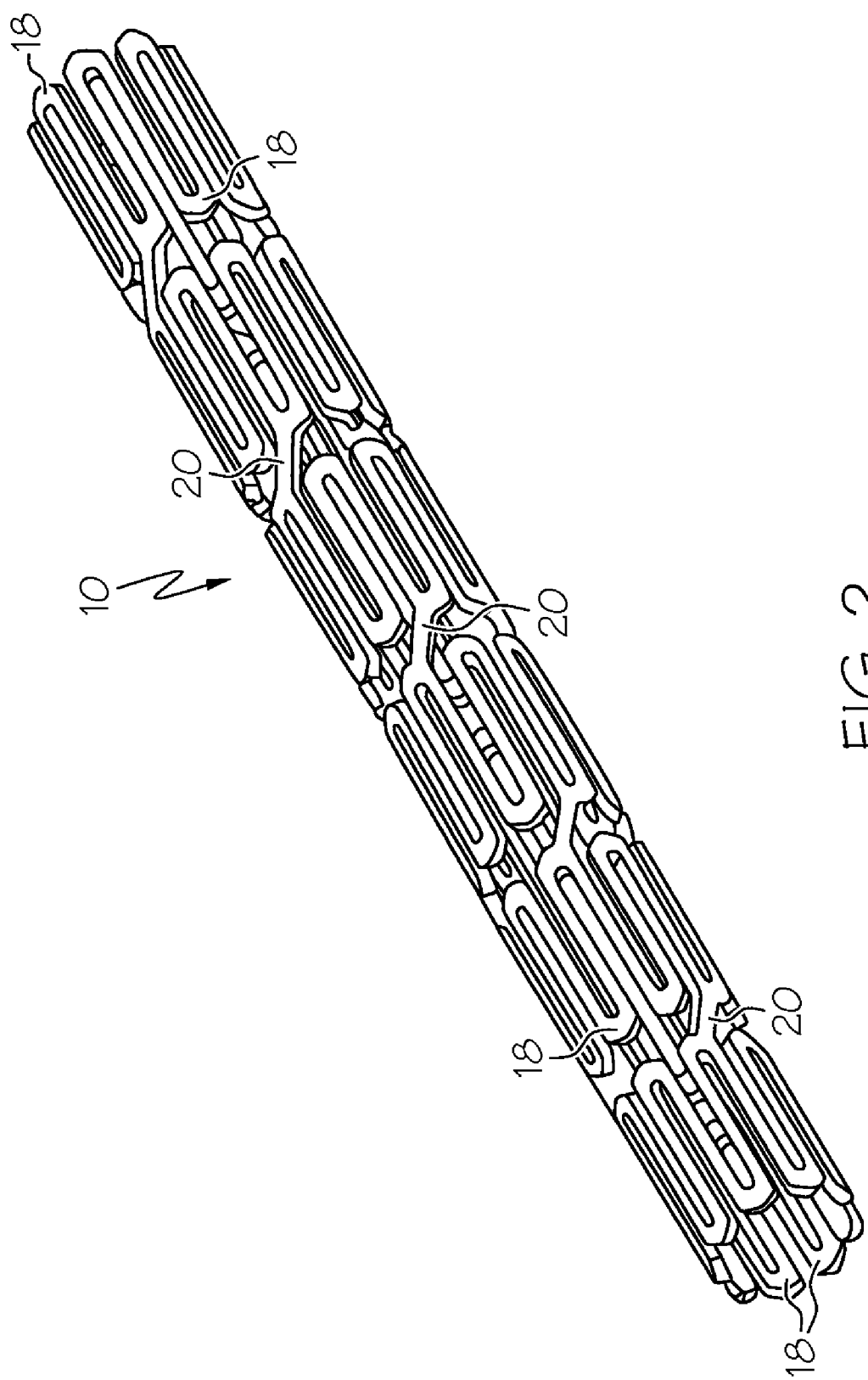
FIG. 2 shows the pattern of FIG. 1 in a tubular, unexpanded stent.

Turning to the Figures, FIG. 1 and FIG. 2 show a fragmentary flat view of an unexpanded stent configuration and the actual tubular stent (unexpanded), respectively. That is, the stent is shown for clarity in FIG. 1 in the flat and may be made from a flat pattern 10 (FIG. 1) which is formed into a tubular shape by rolling the pattern so as to bring edges 12 and 14 together (FIG. 1). The edges may then joined as by welding or the like to provide a configuration such as that shown in FIG. 2.

The configuration can be seen in these Figures to be made up of a plurality of adjacent segments generally indicated at 16, each of which is formed in an undulating flexible pattern of substantially parallel struts 18. Pairs of struts are interconnected at alternating end portions 19a and 19b. As is seen in FIG. 1, the interconnecting end portions 19b of one segment are positioned opposite interconnecting end portions 19a of adjacent segments. The end portions as shown are generally elliptical but may be rounded or square or pointed or the like. Any configuration of end portions is acceptable so long as it provides an undulating pattern, as shown. When the flat form 10 is formed into an unexpanded tube as shown in FIG. 2, the segments are cylindrical but the end portions 19 of adjacent segments remain in an opposed position relative to each other.

Interconnecting elements 20 extend from one end portion 19 of one segment 16 to another end portion 19 of another adjacent segment 16 but not to an oppositely positioned end portion 19 of an adjacent segment 16. This results in the interconnecting elements 20 extending in an angular direction between segments around the periphery of the tubular stent.

In some embodiments, there are at least three struts included between the points on each side of a segment 16 at which an interconnecting element 20 contacts an end portion 19.

Interconnecting elements 20 are preferably of the same length but may vary from one segment to the other. Also, the diagonal direction may reverse from one segment to another extending upwardly in one case and downwardly in another, although all connecting elements between any pair of segments are substantially parallel. FIG. 1, for example shows them extending downwardly, left to right. Upwardly would extend up left to right in this configuration.

Figure 3:
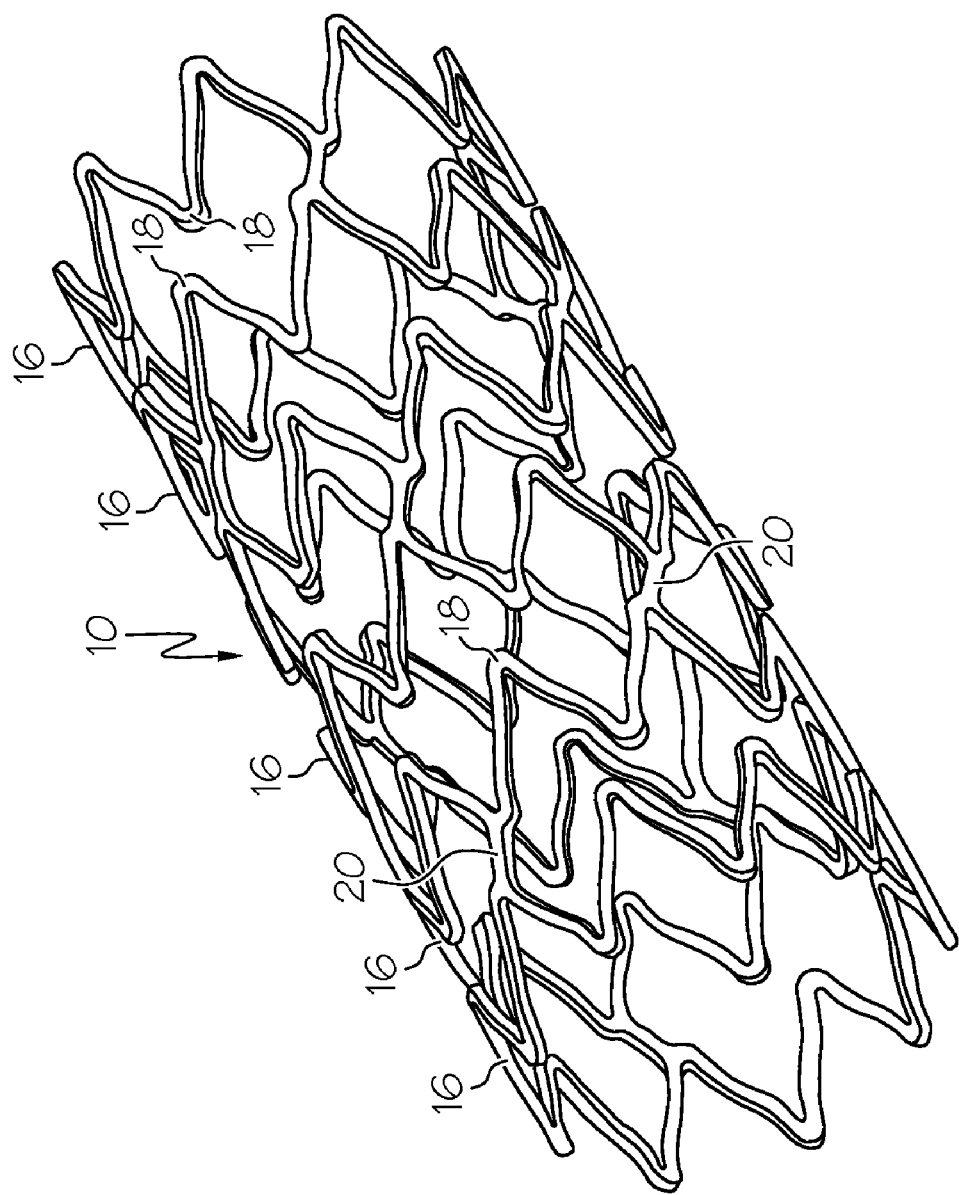
FIG. 3 shows an expanded stent of the embodiment shown in FIG. 1.

As a result of this angular extension of the interconnecting elements 20 between adjacent segments and loops, upon expansion of the stent as seen in FIG. 3, the closest adjacent end portions 19 between segments 16 are displaced from each other and are no longer opposite each other so as to minimize the possibility of binding or overlapping between segments, i.e., pinching.

The number of interconnecting elements 20 may vary depending on circumstances in any particular instance. In some embodiments, a single interconnecting element 20 can span between two adjacent serpentine bands 16. In some embodiments, at least two interconnecting elements 20 can span between two adjacent serpentine bands 16. As shown in FIG. 1, in some embodiments, three interconnecting elements 20 can be used.

Figure 4:
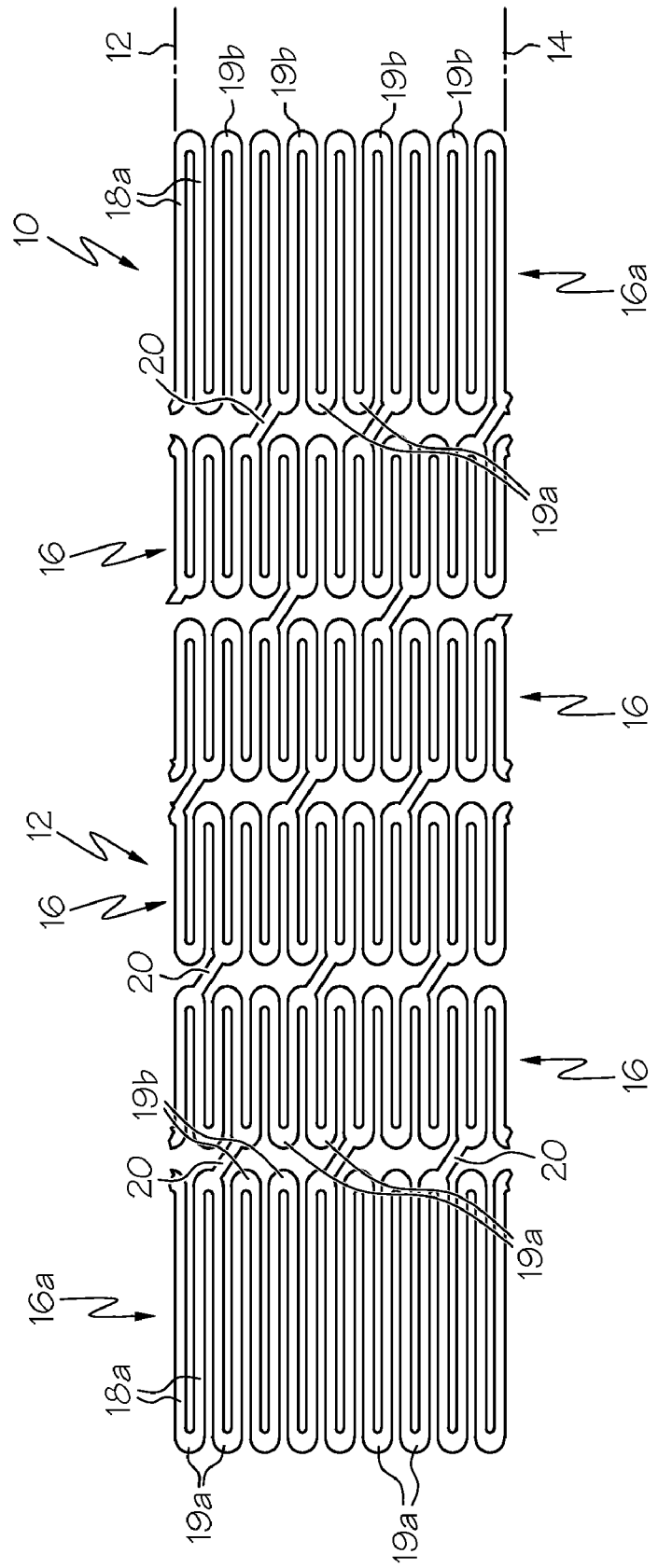
FIG. 4 shows a flat view of an alternate unexpanded stent embodiment.

The alternate design shown in FIG. 4 includes longer struts 18a in the two end segments 16a than in the intermediate segments 16. This allows the end segments (16a) to have less compression resistance than the intermediate segments (16), providing a more gradual transition from the native vessel to the support structure of the stent. Otherwise, the configuration is the same as that shown in FIG. 1.

In some embodiments, the segments 16 can also be described as serpentine bands. The interconnecting elements 20 can also be described as connector struts. The end portions 19 can also be described as turns. End portions 19a can also be described as proximal peaks. End portions 19b can also be described as distal valleys.

Figure 5:
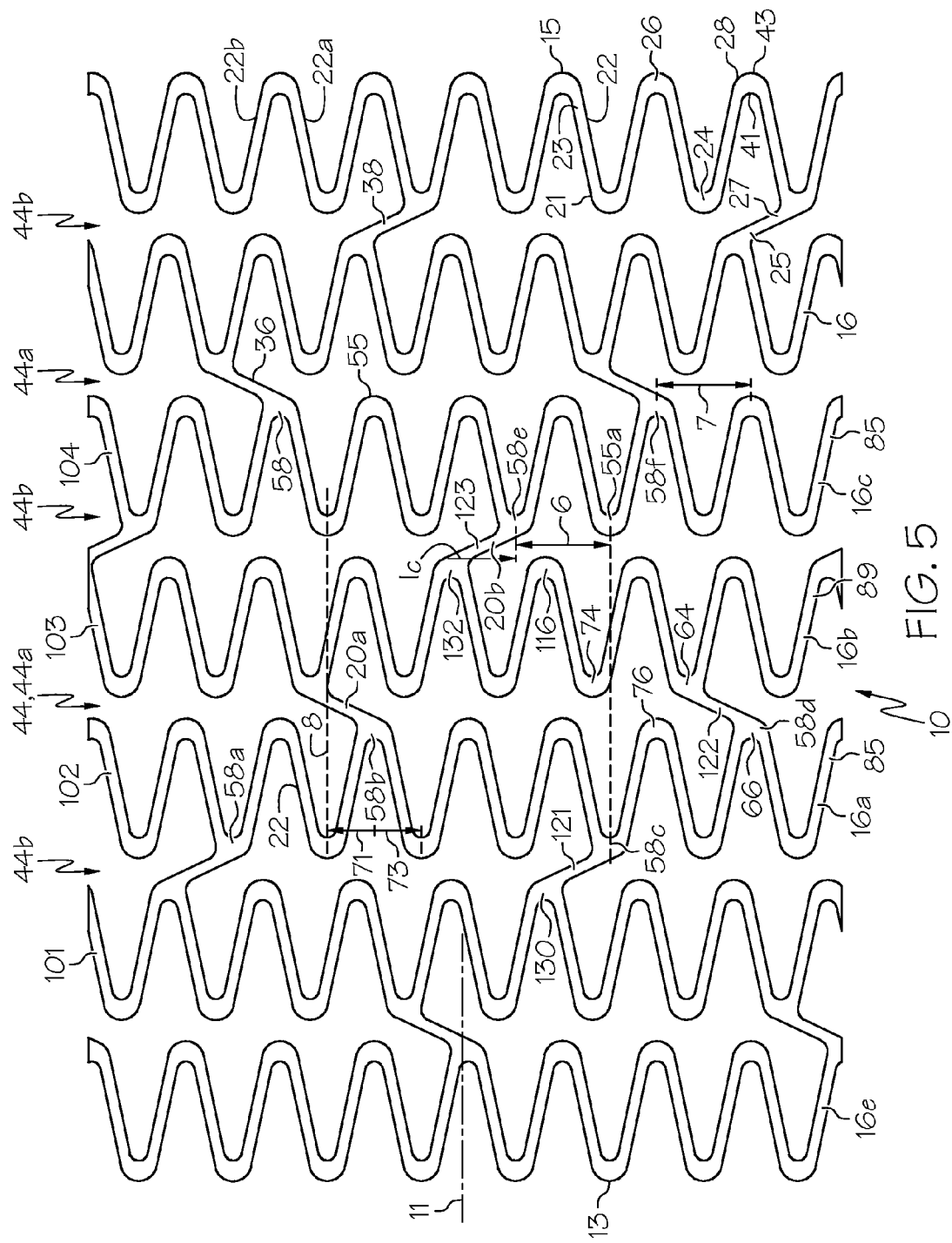
FIG. 5 shows a flat pattern for another embodiment of a stent.

FIG. 5 shows a flat pattern for another embodiment of a stent 10 having a proximal end 13, a distal end 15 and a plurality of serpentine bands 16. Each serpentine band 16 comprises a plurality of band struts 22 and a plurality of turns 28. The band struts 22 and the turns 28 alternate as the serpentine band 16 is traversed. Thus, each band strut 22 has a first end 21 connected to one turn 28 and a second end 23 connected to another turn 28. Each turn 28 connects between two band struts 22 that are adjacent to one another in a stent circumferential direction.

In some embodiments, a band strut 22 is straight along its length as shown in FIG. 5. In some other embodiments, a band strut 22 can include curvature in one or more directions. A serpentine band 16 can further comprise band struts 22 that are shaped differently from one another. Other examples of possible configurations of band struts 22 are disclosed in US Patent Application Publication No. 2002/0095208 and U.S. patent application Ser. No. 11/262,692, the entire disclosures of which are hereby incorporated herein by reference in their entireties.

The turns 28 of a serpentine band 16 comprise alternating proximal peaks 24 and distal valleys 26. Each proximal peak 24 is generally convex with respect to the proximal end 13 and concave with respect to the distal end 15 of the stent 10. Each distal valley 26 is generally convex with respect to the distal end 15 and concave with respect to the proximal end 13 of the stent 10. Each turn 28 further comprises an inner side 41 and an outer side 43. Proximal peaks 24 are oriented with the outer side 43 closer to the proximal end 13 of the stent 10 than the inner side 41. Distal valleys 26 are oriented with the outer side 43 closer to the distal end 15 of the stent 10 than the inner side 41.

A stent 10 can have any suitable number of serpentine bands 16. In various embodiments, a serpentine band 16 can have any suitable number of band struts 22 and any suitable number of turns 28.

A serpentine band 16 can span any suitable distance along the length of the stent 10. In some embodiments, a stent 10 can comprise serpentine bands 16 that span different distances. One method for increasing a lengthwise span of a serpentine band 16 is to increase the length of the band struts 22.

In some embodiments, the proximal peaks 24 of a given serpentine band 16 are aligned around a common circumference of the stent 10, and the distal valleys 26 are similarly aligned around another common circumference of the stent 10. Each circumference can be oriented orthogonal to a longitudinal axis 11 of the stent 10. When turns 28 are aligned around a circumference, an extremity of the outer side 43 of each turn 28 can abut a common reference circumference. In some other embodiments, various peaks 24 can be offset from other peaks 24 within a given serpentine band 16, and various valleys 26 can be offset from other valleys 26 within the band 16.

Each band strut 22 comprises a width, which may be measured in a direction normal to the length of the strut 22. In some embodiments, all struts 22 within a given serpentine band 16 have the same width. In some embodiments, the width of various struts 22 within a serpentine band 16 can be different from one another. In some embodiments, the width of a strut 22 can change along the length of the strut 22. In some embodiments, the width of struts 22 of one serpentine band 16 can be different from the width of struts 22 of another serpentine band 16.

Each turn 28 has a width, which may be measured in a direction normal to the side of the turn 28 (e.g. normal to a tangent line). In some embodiments, the width of a turn 28 can be greater than the width of one or more struts 22 of the stent 10. In some embodiments, the width of a turn 28 can be less than the width of one or more struts 22 of the stent 10. In some embodiments, the width of a turn 28 varies from one end of the turn 28 to the other. For example, a turn 28 can connect to a strut 22 at one end having the same width as the strut 22. The width of the turn 28 increases, and in some embodiments reaches a maximum at a midpoint of the turn 28. The width of the turn 28 then decreases to the width of another strut 22, which may be connected to the second end of the turn 28.

Serpentine bands 16 that are adjacent to one another along the length of the stent 10 are connected by at least one connector strut 20. In some embodiments, a connector strut 20 spans between turns 28 of adjacent serpentine bands 16. For example, a first end 25 of a connector strut 20 can connect to a distal valley 26 of one serpentine band 16, and a second end 27 of the connector strut 20 can connect to a proximal peak 24 of an adjacent serpentine band 16.

Connector struts 20 can connect to any portion of a serpentine band 16. In some embodiments, a connector strut 20 connects to a turn 28 as shown in FIG. 5. In some embodiments, a connector strut 20 can connect to a band strut 22.

In some embodiments, a connector strut 20 is linear or straight along its length. In some embodiments, a connector strut 20 can include curvature along its length, and can further include multiple portions of curvature, for example a convex portion and a concave portion that may be connected at an inflection point.

Each connector strut 20 comprises a width, which may be measured in a direction normal to the length of the strut 20. In some embodiments, every connector strut 20 has the same width. In some other embodiments, a connector strut 20 can have a width that is different from another connector strut 20. In some embodiments, the width of a connector strut 20 can change along the length of the strut 20.

Some further examples of configurations that can be used for connector struts 16 are disclosed in U.S. Pat. Nos. 6,261, 319 and 6,478,816, and US Published Patent Application No. 20040243216, the entire disclosures of which are hereby incorporated herein by reference.

In some embodiments, connector struts 20 comprise a first type of connector strut 36 and a second type of connector strut 38. A first connector strut 36 extends in a first direction. The first connector strut 36 can be oriented at a first angle to a stent lengthwise axis 11. A second connector strut 38 extends in a second direction that is different than or non-parallel to the first direction. The second connector strut 38 can be oriented at a second angle to a stent lengthwise axis 11. In some embodiments, the first angle and the second angle can have the same magnitude but different orientations. For example, a first connector strut 36 can form a 70° angle with a stent lengthwise axis 11, while a second connector strut 38 can form a negative 70° angle with the stent lengthwise axis 11. In some embodiments, a first angle may comprise a mirror image of a second angle across a line parallel to the stent lengthwise axis 11. In some embodiments, first type of connector strut 36 can have a different shape than second type of connector strut 38.

In some embodiments, an area of the stent 10 located between two adjacent serpentine bands 16 can be considered a connector column 44. Each connector column 44 comprises a plurality of connector struts 20. In some embodiments, each connector strut 20 in a connector column 44 can be similar to one another. For example, each connector strut 20 in a first connector column 44a can comprise a first type of connector strut 36. Each connector strut 20 in a second connector column 44b can comprise a second type of connector strut 38.

In some embodiments, first connector columns 44a and second connector columns 44b can alternate along the length of the stent 10. Thus, each interior serpentine band 16 can be positioned between a first connector column 44a and a second connector column 44b. Accordingly, connector struts 20 that connect to one side of a serpentine band 16 can comprise first connector struts 36, and connector struts 20 that connect to the other side of the serpentine band 16 can comprise second connector struts 38.

Turns 28 can comprise connected turns 58 or unconnected turns 55 depending upon whether the turn 28 connects to a connector strut 20. Similarly, proximal peaks 24 can comprise connected proximal peaks 64 or unconnected proximal peaks 74, and distal valleys 26 can comprise connected distal valleys 66 or unconnected distal valleys 76.

A serpentine band 16 can have more unconnected turns 55 than connected turns 58. In some embodiments, a serpentine band 16 has three unconnected turns 55 for each connected turn 58. The 3:1 ratio of unconnected turns 55 to connected turns 58 can also apply to the proximal peaks 24 and to the distal valleys 26.

In some embodiments, as a serpentine band 16 is traversed, there is a repeating pattern of x number of unconnected turns 55 between one connected turn 58 and the next connected turn 58, and then y number of unconnected turns until the next connected turn 58, wherein y is greater than x. For example, referring to FIG. 5, as a serpentine band 16a is traversed from a first connected turn 58a to a second connected turn 58b, there are two unconnected turns 55. Thus, x can equal two. As the serpentine band 16a is traversed from the second connected turn 58b to a third connected turn 58c, there are four unconnected turns 55. Thus, y can equal four. The pattern will then repeat, with x=2 unconnected turns 55 between the third connected turn 58c and a fourth connected turn 58d, etc. In some embodiments, y is a multiple of x, for example y=2x.

In some embodiments, starting from a connected turn 58, a serpentine band 16 can comprise three band struts 22 between the connected turn 58 and the next connected turn 58 in a first direction. The serpentine band 16 can further comprise five band struts 22 between the connected turn 58 and the next connected turn 58 in a second direction. For example, referring to FIG. 5, a serpentine band 16a includes three band struts 22 between a connected turn 58b and the next connected turn 58a in a first circumferential direction 71. The serpentine band 16a also includes five band struts 22 between the connected turn 58b and the next connected turn 58c in a second circumferential direction 73.

In some embodiments, as a serpentine band 16 is traversed, there can be a repeating pattern of three band struts 22 between one connected turn 58 and the next connected turn 58, and then five band struts 22 until the next connected turn 58. For example, referring to FIG. 5, as a serpentine band 16a is traversed from a first connected turn 58a to a second connected turn 58b, there are three band struts 22. As the serpentine band 16a is traversed from the second connected turn 58b to a third connected turn 58c, there are five band struts 22. The pattern will then repeat, with three band struts 22 between the third connected turn 58c and a fourth connected turn 58d, etc.

In some embodiments, an end serpentine band 16e that is located on the proximal end 13 or the distal end 15 of the stent 10 comprises seven unconnected turns 55 between two connected turns 58. The end serpentine band 16e can further comprise eight band struts 22 between two connected turns 58.

In some embodiments, the connector struts 20 of adjacent connector columns 44 are offset from one another in a stent circumferential direction. For example, one connector strut 20a is offset in a stent circumferential direction from another connector strut 20b located in an adjacent connector column 44. Thus, in some embodiments, a reference line 8 oriented parallel to the stent longitudinal axis 11 that intersects one connector strut 20a will not intersect the other connector strut 20b.

The band struts 22 of a serpentine band 16 can comprise alternating first band struts 22a and second band struts 22b. In some embodiments, each first band strut 22a is parallel to one another as shown in the flat pattern of FIG. 5. Each second band strut 22b is parallel to one another and non-parallel to the first band struts 22a.

Serpentine bands 16 can comprise a first type of serpentine band 85 and a second type of serpentine band 89. In some embodiments, each first type of serpentine band 85 is aligned with one another such that similar portions of each band 85 align along the length of the stent 10. Each second type of serpentine band 89 is aligned with one another such that similar portions of each band 89 align along the length of the stent 10. Each first type of serpentine band 85 is offset from each second type of serpentine band 89 such that similar portions of the different types of bands 85, 89 are not aligned along the length of the stent.

In some embodiments, the first type of serpentine band 85 and the second type of serpentine band 89 can alternate along the length of the stent 10. Thus, serpentine bands 16 that are located adjacent to one another along the length of the stent 10 can be offset from one another in a stent circumferential direction. Every other serpentine band 16 can be aligned with one another in a stent circumferential direction. For example, a stent 10 can comprise a first serpentine band 16a, a second serpentine band 16b and a third serpentine band 16c along its length. The first and third serpentine bands 16a, 16c comprise a first type of serpentine band 85, and the second serpentine band 16b comprises a second type of serpentine band 89. The first serpentine band 16a is offset from the second serpentine band 16b in a stent circumferential direction. Thus, a reference line 8 extending parallel to the stent longitudinal axis 11 will not intersect similar portions of the first serpentine band 16a and the second serpentine band 16b. As shown, the reference line 8 bisects a proximal peak 24 of the first serpentine band 16a but does not bisect a proximal peak 24 of the second serpentine band 16b. The second serpentine band 16b is similarly offset from the third serpentine band 16c. The first serpentine band 16a and the third serpentine band 16c are aligned with one another in a stent circumferential direction. Thus, the reference line 8 bisects a proximal peak 24 of both the first serpentine band 16a and the third serpentine band 16c.

One serpentine band 16 of a given type 85, 89 can have connected turns 58 that are aligned with unconnected turns 55 of another serpentine band 16 of the same type 85, 89 along the length of the stent 10. For example, the first serpentine band 16a of FIG. 5 includes a connected turn 58c that is longitudinally aligned with an unconnected turn 55a of the third serpentine band 16c.

One serpentine band 16 of a given type 85, 89 can have connected turns 58 that are offset from connected turns 58 of the next adjacent serpentine band 16 of the same type 85, 89 by one proximal peak or one distal valley. For example, the first serpentine band 16a of FIG. 5 includes a connected proximal peak 58c that is offset 6 from a connected proximal peak 58e of the third serpentine band 16c by one proximal peak 24. Similarly, the first serpentine band 16a includes a connected distal valley 58d that is offset 7 from a connected distal valley 58f of the third serpentine band 16c by one distal valley 26. Thus, in some embodiments, the connector struts 20 of adjacent similar types of connector columns 44a, 44b are offset from one another in the stent circumferential direction by an amount equal to the spacing 6, 7 between adjacent proximal peaks 24 or between adjacent distal valleys 26.

Referring to FIGS. 1 and 5, in some embodiments, a stent comprises at least a first serpentine band 101, a second serpentine band 102, a third serpentine band 103 and a fourth serpentine band 104. Each serpentine band 101-104 comprises connected proximal peaks 64, unconnected proximal peaks 74, connected distal valleys 66 and unconnected distal valleys 76. Each serpentine band 101-104 includes at least two unconnected proximal peaks 74 for each connected proximal peak 64, and at least two unconnected distal valleys 76 for each connected distal valley 66.

A first connector strut 121 connects between a first connected distal valley 130, located on the first serpentine band 101, and a connected proximal peak 64 of the second serpentine band 102. A second connector strut 122 connects between the second serpentine band 102 and the third serpentine band 103. A third connector strut 123 connects between a second connected distal valley 132, located on the third serpentine band 103, and a connected proximal peak 64 of the fourth serpentine band 104.

The first connected distal valley 130 is circumferentially aligned with a first unconnected distal valley 116 of the third serpentine band 103. The first unconnected distal valley 116 is directly adjacent in a circumferential direction to the second connected distal valley 132.

Each connected distal valley 66 of the first serpentine band 101 is circumferentially aligned with an unconnected distal valley 76 of the third serpentine band 103. Further, each unconnected distal valley 76 of the third serpentine band 103 that is circumferentially aligned with a connected distal valley 66 of the first serpentine band 101 is offset from a connected distal valley 66 of the third serpentine band 103 in a circumferential direction by one distal valley (e.g. spacing 7 as shown on FIG. 5).

The third connector strut 123 is oriented at a non-zero angle to the stent longitudinal axis 11 and thus comprises a circumferential length component $l_c$ oriented in a stent circumferential direction. The circumferential length component $l_c$ extends from the second connected distal valley 132 in a circumferential direction toward the first unconnected distal valley 116. Thus, in some embodiments, connector struts 20 that connect to connected distal valleys 66 of the third serpentine band 103 extend at an angle to the stent longitudinal axis 11, wherein the angle is oriented in the direction of an adjacent unconnected distal valley 76 (e.g. distal valley 116) that is circumferentially aligned with a connected distal valley 66 (e.g. distal valley 130) of the first serpentine band 101.

The second serpentine band 102 comprises three band struts 22 between the first connector strut 121 and the second connector strut 122. Thus, there are three band struts 22 located between the connected distal valley 66 that connects to the first connector strut 121 and the connected proximal peak 64 that connects to the second connector strut 122.

Each connected distal valley 66 of the second serpentine band 102 is circumferentially aligned with an unconnected distal valley 76 of the fourth serpentine band 104. Further, each unconnected distal valley 76 of the fourth serpentine band 104 that is circumferentially aligned with a connected distal valley 66 of the second serpentine band 102 is offset from a connected distal valley 66 of the fourth serpentine band 104 in a circumferential direction by one distal valley (e.g. spacing 7 as shown on FIG. 5).

Figure 6:
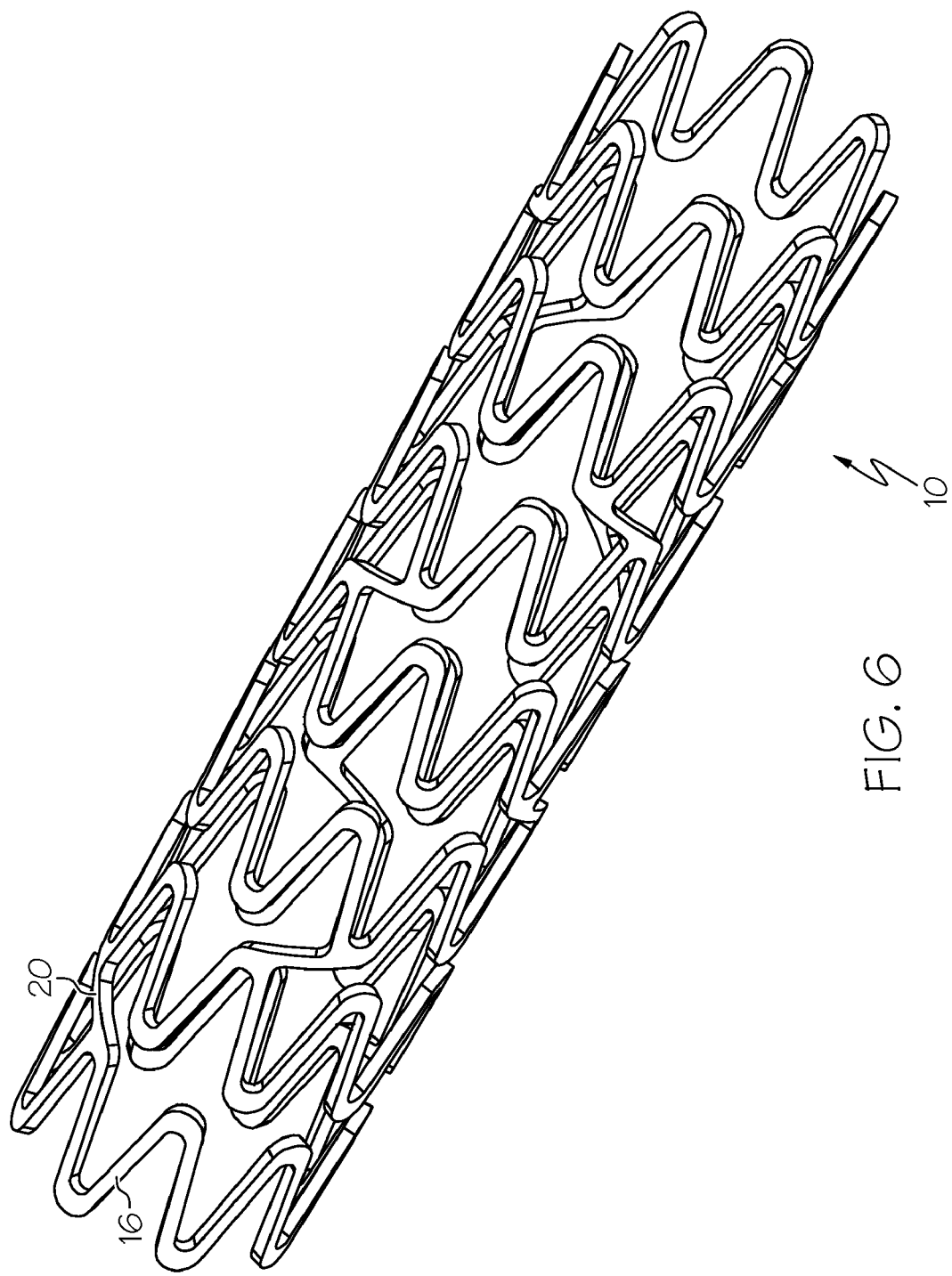
FIG. 6 shows a three-dimensional isometric view of an embodiment of a stent.

FIG. 6 shows a three-dimensional substantially cylindrical stent 10 according to the flat pattern shown in FIG. 5. The stent 10 is shown at a nominal state of expansion and could be further reduced in diameter, for example being crimped onto a delivery catheter, or could be further expanded.

Figure 7:
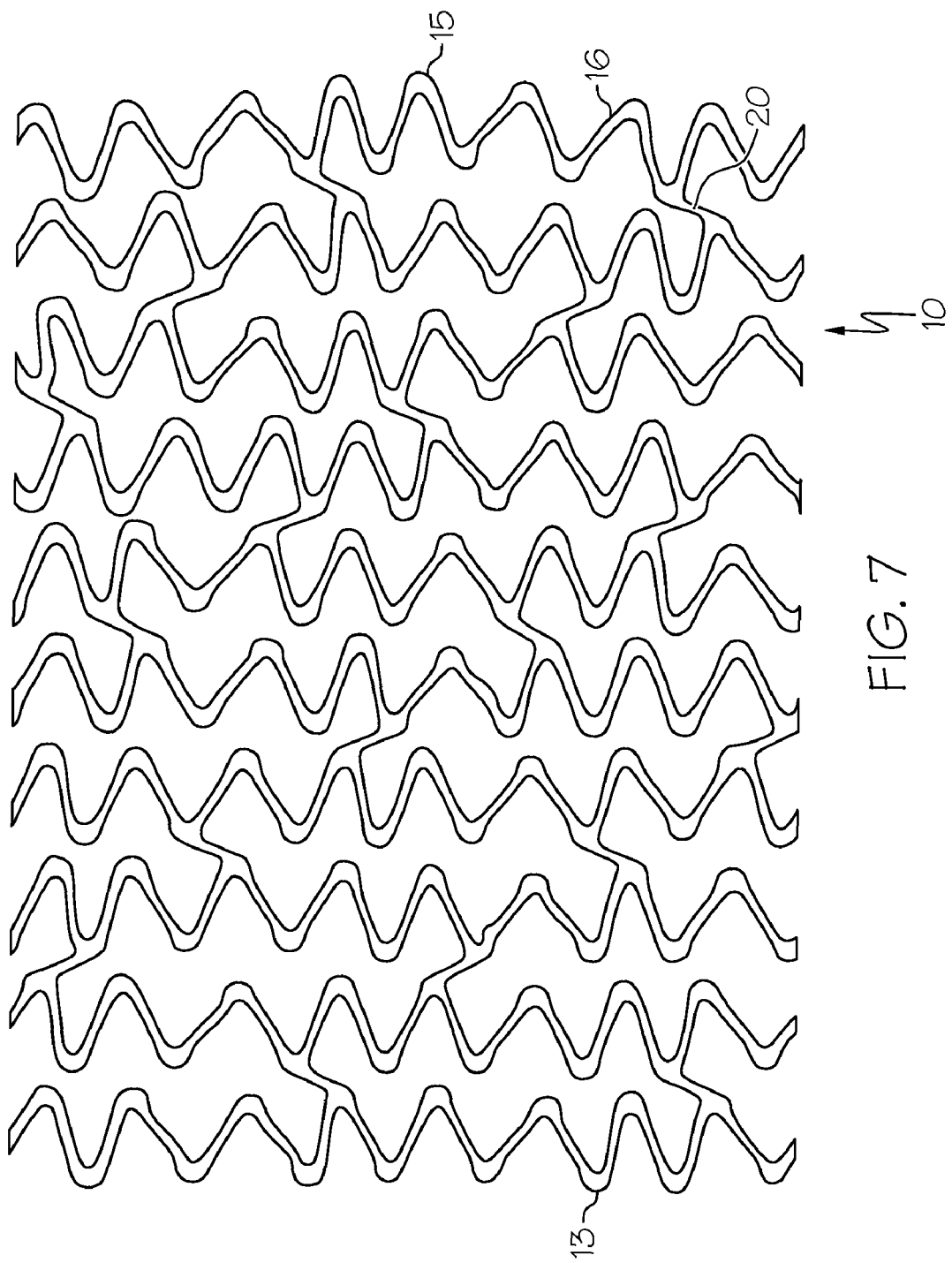
FIG. 7 shows a flat pattern depiction of a stent pattern similar to the pattern of FIG. 5, in a state of expansion that is greater than that depicted in FIG. 5.

FIG. 7 shows an example of a stent 10 in a state of expansion that is greater than that of FIG. 5.

Figure 8:
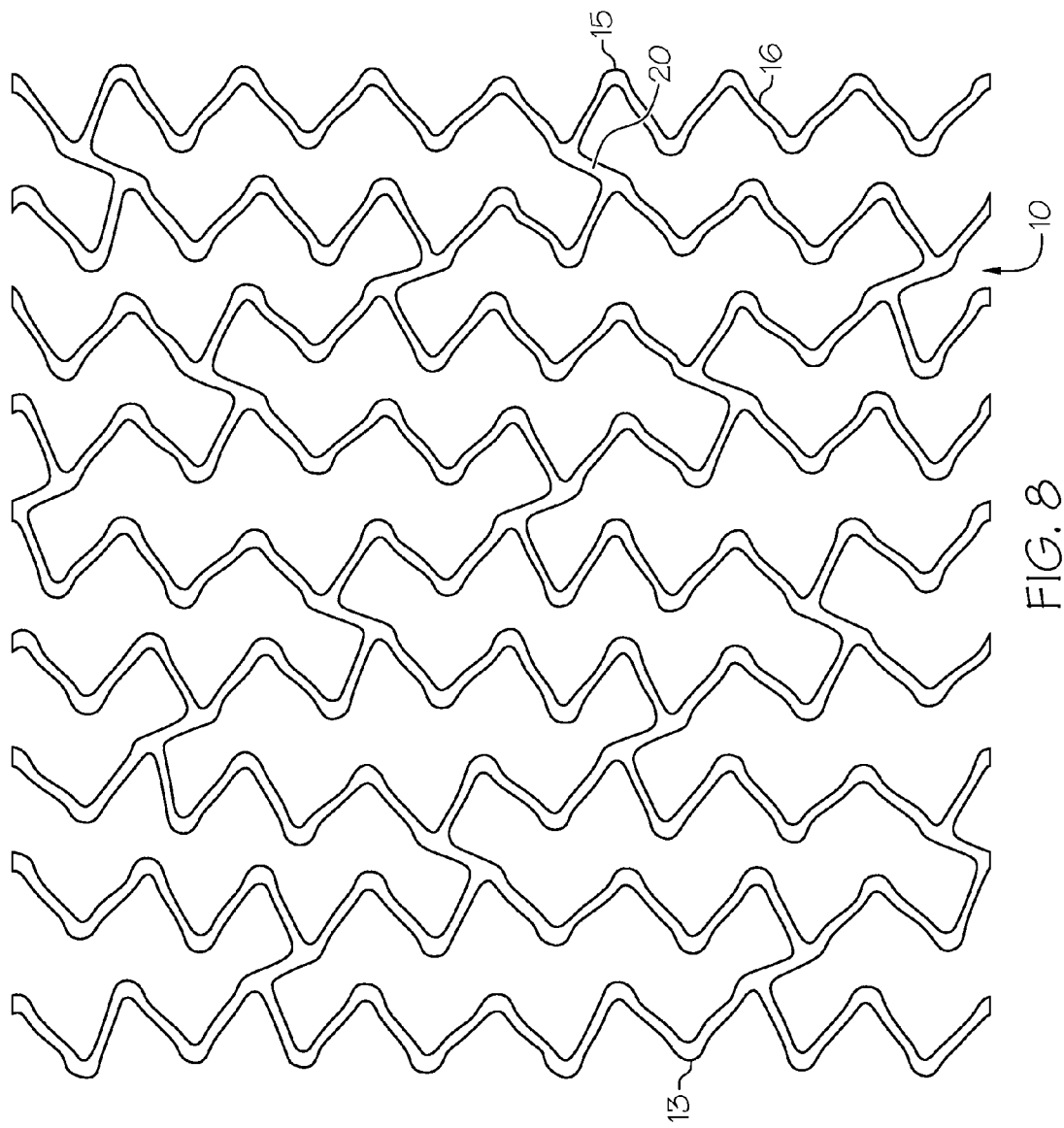
FIG. 8 shows a flat pattern depiction of a stent pattern similar to the pattern of FIG. 7, in a state of expansion that is greater than that depicted in FIG. 7.

FIG. 8 shows an example of a stent 10 in a state of expansion that is greater than that of FIG. 7.

Figure 9:
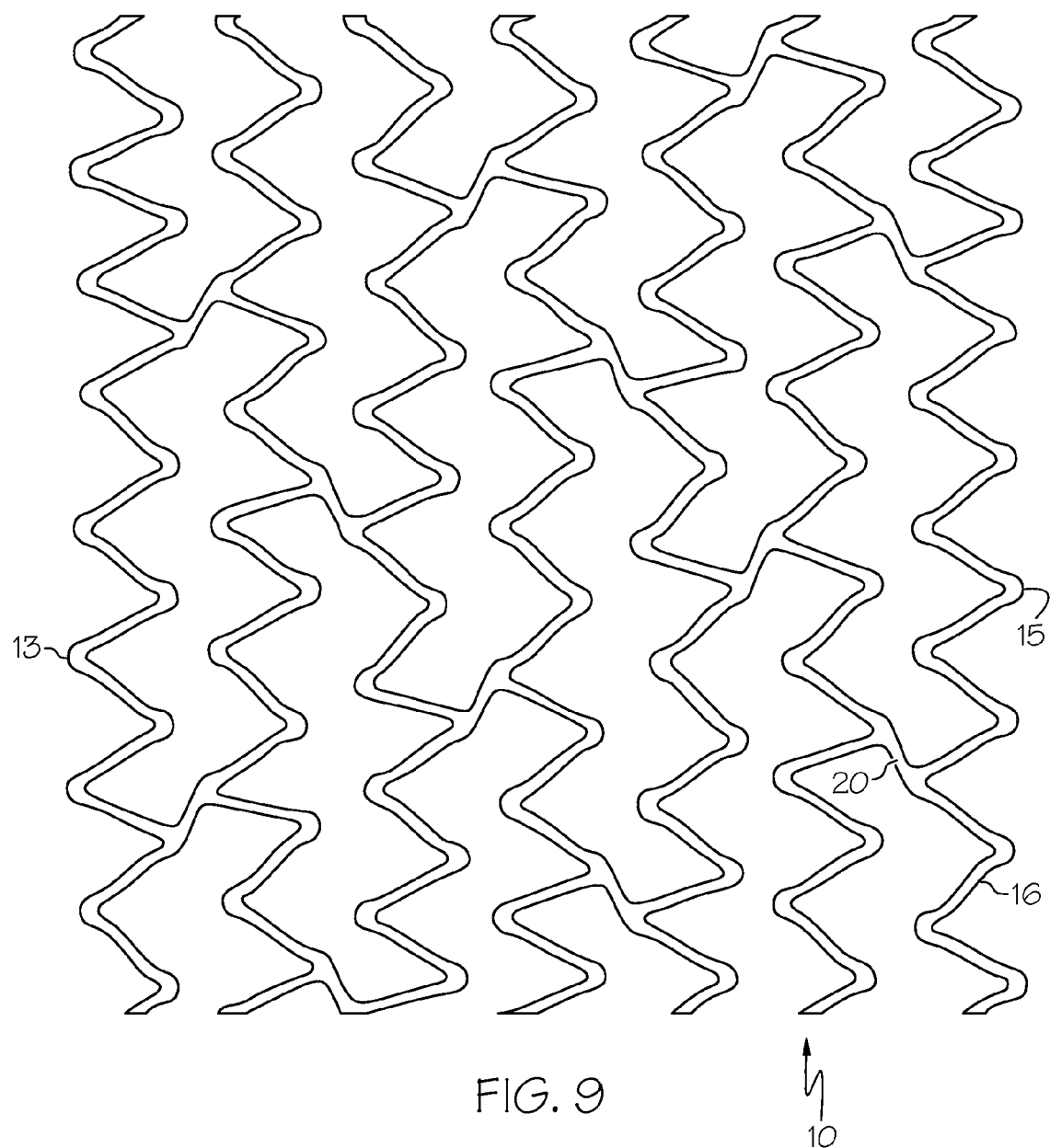
FIG. 9 shows a flat pattern depiction of a stent pattern similar to the pattern of FIG. 8, in a state of expansion that is greater than that depicted in FIG. 8.

FIG. 9 shows an example of a stent 10 in a state of expansion that is greater than that of FIG. 8.

Figure 10:
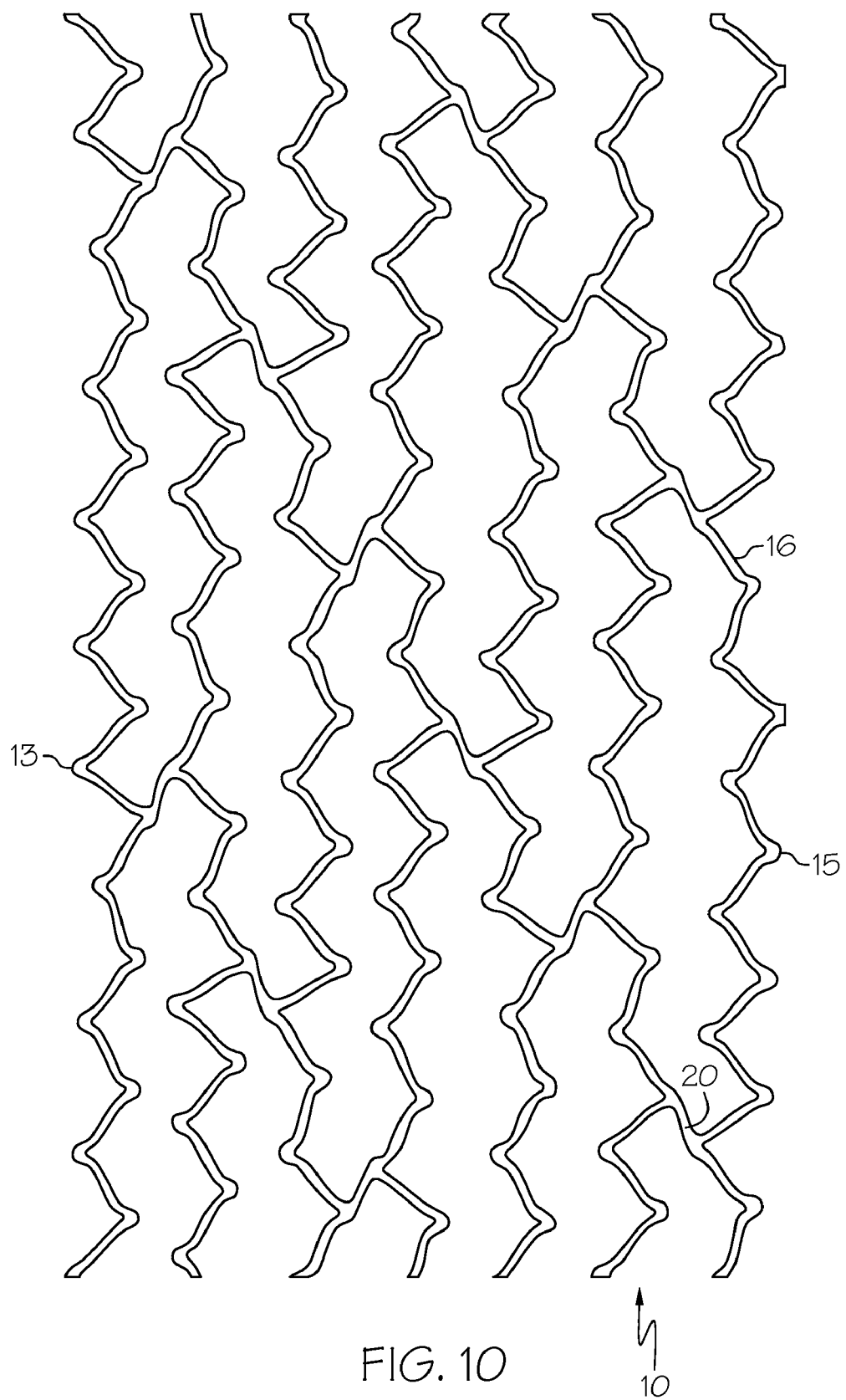
FIG. 10 shows a flat pattern depiction of a stent pattern similar to the pattern of FIG. 9, in a state of expansion that is greater than that depicted in FIG. 9. The state of expansion shown can be considered a state of overexpansion.

FIG. 10 shows an example of a stent 10 in a state of expansion that is greater than that of FIG. 9. The amount of expansion depicted can be described as a state of overexpansion. Generally, a stent 10 that is actually used in a bodily vessel will be subject to less expansion than the amount shown in FIG. 10. However, the stent 10 pattern shown is capable of providing vessel support even in a substantially overexpanded state.

Figure 11:
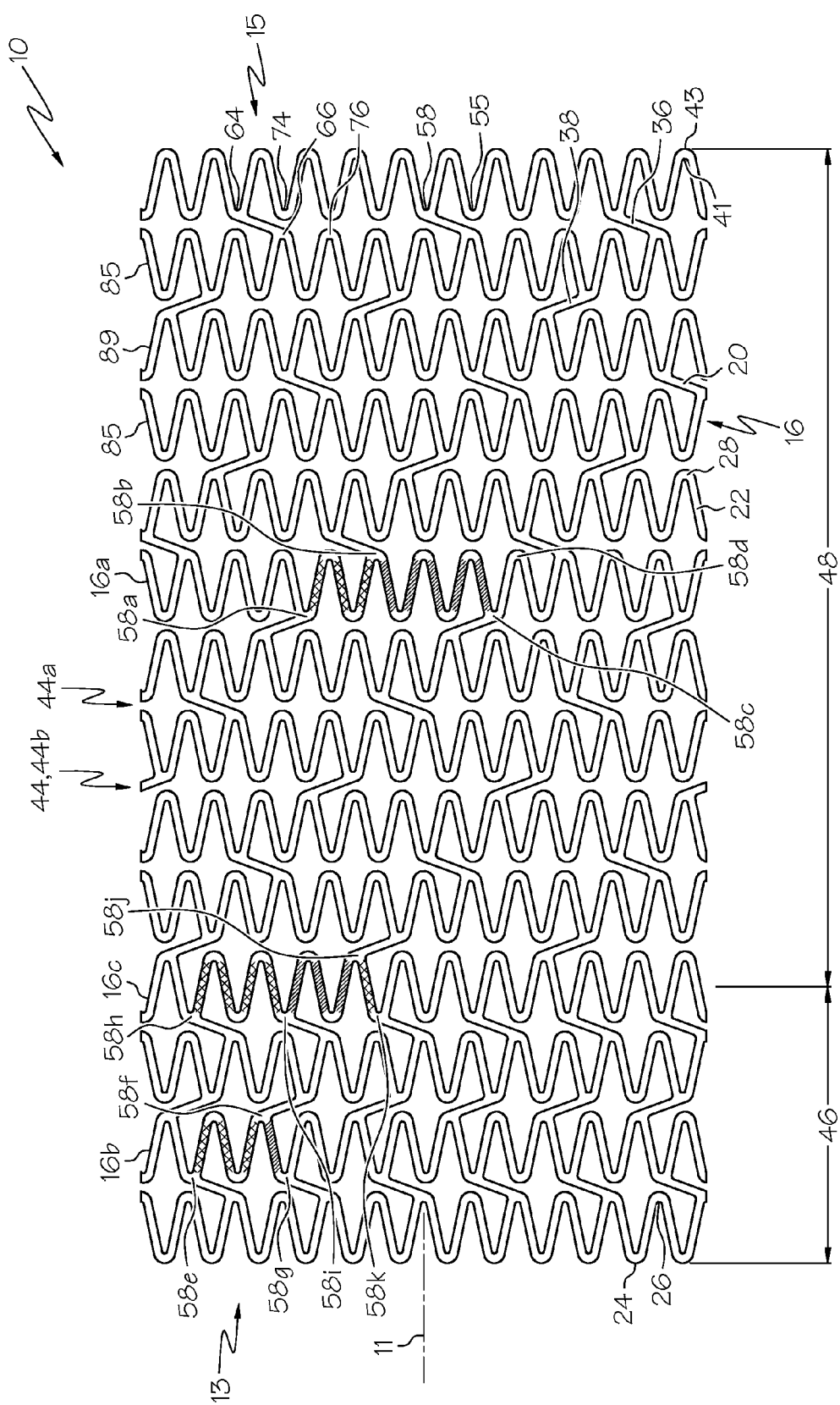
FIG. 11 shows a flat pattern for another embodiment of a stent.

FIG. 11 shows a flat pattern for another embodiment of a stent 10 having a proximal end 13, a distal end 15 and a plurality of serpentine bands 16. Adjacent serpentine bands 16 are connected across a connector column 44 by a plurality of connector struts 20.

The turns 28 of a serpentine band 16 comprise alternating proximal peaks 24 and distal valleys 26. Each turn 28 can comprise a connected turn 58 or an unconnected turn 55 depending upon whether the turn 28 connects to a connector strut 20. Similarly, proximal peaks 24 can comprise connected proximal peaks 64 or unconnected proximal peaks 74, and distal valleys 26 can comprise connected distal valleys 66 or unconnected distal valleys 76.

In some embodiments, a stent 10 comprises a first portion 46 and a second portion 48. Each portion 46, 48 can comprise a portion of the length of the stent 10. In some embodiments, a connector column 44 located in the first portion 46 comprises more connector struts 20 than a connector column 44 located in the second portion 48. In some embodiments, a connector column 44 located in the first portion 46 comprises twice as many connector struts 20 as a connector column 44 located in the second portion 48. In some embodiments, each connector column 44 located in the first portion 46 comprises more connector struts 20 than each connector column 44 located in the second portion 48.

In some embodiments, the first portion 46 comprises at least two connector columns 44. In some embodiments, the first portion 46 comprises at least three connector columns 44.

In some embodiments, the second portion 48 comprises more connector columns 44 than the first portion 46. In some embodiments, the second portion 48 comprises at least twice as many connector columns 44 as the first portion 46. In some embodiments, the second portion 48 comprises at least three times as many connector columns 44 as the first portion 46.

In some embodiments, the second portion 48 comprises at least one serpentine band 16 that comprises a repeating pattern of three band struts 22 and then five band struts 22 extending between connected turns 58 as the serpentine band 16 is traversed (3, 5; 3, 5; 3, 5). Thus, referring to FIG. 11 and a first serpentine band 16a, starting from a first connected turn 58a, the serpentine band 16a can comprise three band struts 22 between the first connected turn 58a and a second connected turn 58b, wherein the first and second connected turns 58a, 58b can be considered "adjacent" connected turns 58 within the serpentine band 16a as the serpentine band 16a is traversed. The serpentine band 16a can further comprise five band struts 22 between the second connected turn 58b and a third connected turn 58c. The pattern can then repeat, with three band struts 22 between the third connected turn 58c and a fourth connected turn 58d, etc.

In some embodiments, the second portion 48 comprises a plurality of serpentine bands 16 that have the repeating pattern of three band struts 22 and then five band struts 22 extending between adjacent connected turns 58. In some embodiments, the second portion 48 can comprise at least four, six or eight or more of such serpentine bands 16.

A serpentine band 16 can similarly comprise a repeating pattern of two unconnected turns 55 and then four unconnected turns 55 extending between connected turns 58 as the serpentine band 16 is traversed (2, 4; 2, 4; 2, 4). Thus, the first serpentine band 16a can comprise two unconnected turns 55 between the first connected turn 58a and the second connected turn 58b as the serpentine band 16a is traversed. The serpentine band 16a can further comprise four unconnected turns 55 between the second connected turn 58b and the third connected turn 58c. The pattern can then repeat, with two unconnected turns 55 between the third connected turn 58c and the fourth connected turn 58d, etc.

In some embodiments, the first portion 46 comprises at least one serpentine band 16 that comprises a repeating pattern of three band struts 22 and then one band strut 22 extending between connected turns 58 as the serpentine band 16 is traversed (3, 1; 3, 1; 3, 1). Thus, a second serpentine band 16b can comprise three band struts 22 between a first connected turn 58e and a second connected turn 58f, and can further comprise one band strut 22 between the second connected turn 58f and a third connected turn 58g. The pattern can then repeat, with three band struts 22 between the third connected turn 58g and the next connected turn 58, etc.

In some embodiments, the first portion 46 comprises a plurality of serpentine bands 16 that have the repeating pattern of three band struts 22 and then one band strut 22 extending between adjacent connected turns 58. In some embodiments, the first portion 46 can comprise at least two or three or more of such serpentine bands 16.

A serpentine band 16 can similarly comprise a repeating pattern of two unconnected turns 55 and then zero unconnected turns 55 extending between connected turns 58 as the serpentine band 16 is traversed (2, 0; 2, 0; 2, 0). Thus, the second serpentine band 16b can comprise two unconnected turns 55 between the first connected turn 58e and the second connected turn 58f as the serpentine band 16b is traversed. The serpentine band 16b can further comprise zero unconnected turns 55 between the second connected turn 58f and the third connected turn 58g. The pattern can then repeat, with two unconnected turns 55 between the third connected turn 58g and the next connected turn 58, etc. This pattern can also be described as a repeating pattern of two connected turns 58 and then two unconnected turns 55 as the serpentine band 16b is traversed.

In some embodiments, a stent 10 further comprises at least one serpentine band 16 that comprises a repeating pattern of four band struts 22, then three band struts 22 and then one band strut 22 extending between connected turns 58 as the serpentine band 16 is traversed (4, 3, 1; 4, 3, 1; 4, 3, 1). Thus, a third serpentine band 16c can comprise four band struts 22 between a first connected turn 58h and a second connected turn 58i, three band struts 22 between the second connected turn 58i and a third connected turn 58j, and one band strut 22 between the third connected turn 58j and a fourth connected turn 58k. The pattern can then repeat, with four band struts 22 between the fourth connected turn 58k and the next connected turn 58, etc. In some embodiments, such a serpentine band 16c can comprise a transitional band between the first portion 46 and the second portion 48 of the stent 10.

A serpentine band 16c can similarly comprise a repeating pattern of three unconnected turns 55, then two unconnected turns 55 and then zero unconnected turns 55 extending between connected turns 58 as the serpentine band 16c is traversed (3, 2, 0; 3, 2, 0; 3, 2, 0). Thus, the third serpentine band 16c can comprise three unconnected turns 55 between the first connected turn 58h and the second connected turn 58i as the serpentine band 16c is traversed. The serpentine band 16c can further comprise two unconnected turns 55 between the second connected turn 58i and the third connected turn 58j, and zero unconnected turns 55 between the third connected turn 58j and the fourth connected turn 58k. The pattern can then repeat, with three unconnected turns 55 between the fourth connected turn 58k and the next connected turn 58, etc. This pattern can also be described as a repeating pattern of two connected turns 58, three unconnected turns 55, one connected turn 58, and then two unconnected turns 55 as the serpentine band 16c is traversed.

Serpentine bands 16 can comprise a first type of serpentine band 85 and a second type of serpentine band 89. In some embodiments, each first type of serpentine band 85 is aligned with one another such that similar portions of each band 85 align along the length of the stent 10. For example, a proximal peak 24 of a first type of serpentine band 85 can be aligned with a proximal peak 24 of another first type of serpentine band 85 in a direction parallel to the stent longitudinal axis 11. Each second type of serpentine band 89 is aligned with one another such that similar portions of each band 89 align along the length of the stent 10. For example, a proximal peak 24 of a second type of serpentine band 89 can be aligned with a proximal peak 24 of another second type of serpentine band 89 in a direction parallel to the stent longitudinal axis 11. Each first type of serpentine band 85 can be offset from each second type of serpentine band 89 such that similar portions of the different types of bands 85, 89 are not aligned along the length of the stent. A proximal peak 24 of a first type of serpentine band 85 can further be aligned with a distal valley 26 of a second type of serpentine band 89 in a direction parallel to the stent longitudinal axis 11.

In some embodiments, the first type of serpentine band 85 and the second type of serpentine band 89 can alternate along the length of the stent 10.

Figure 12:
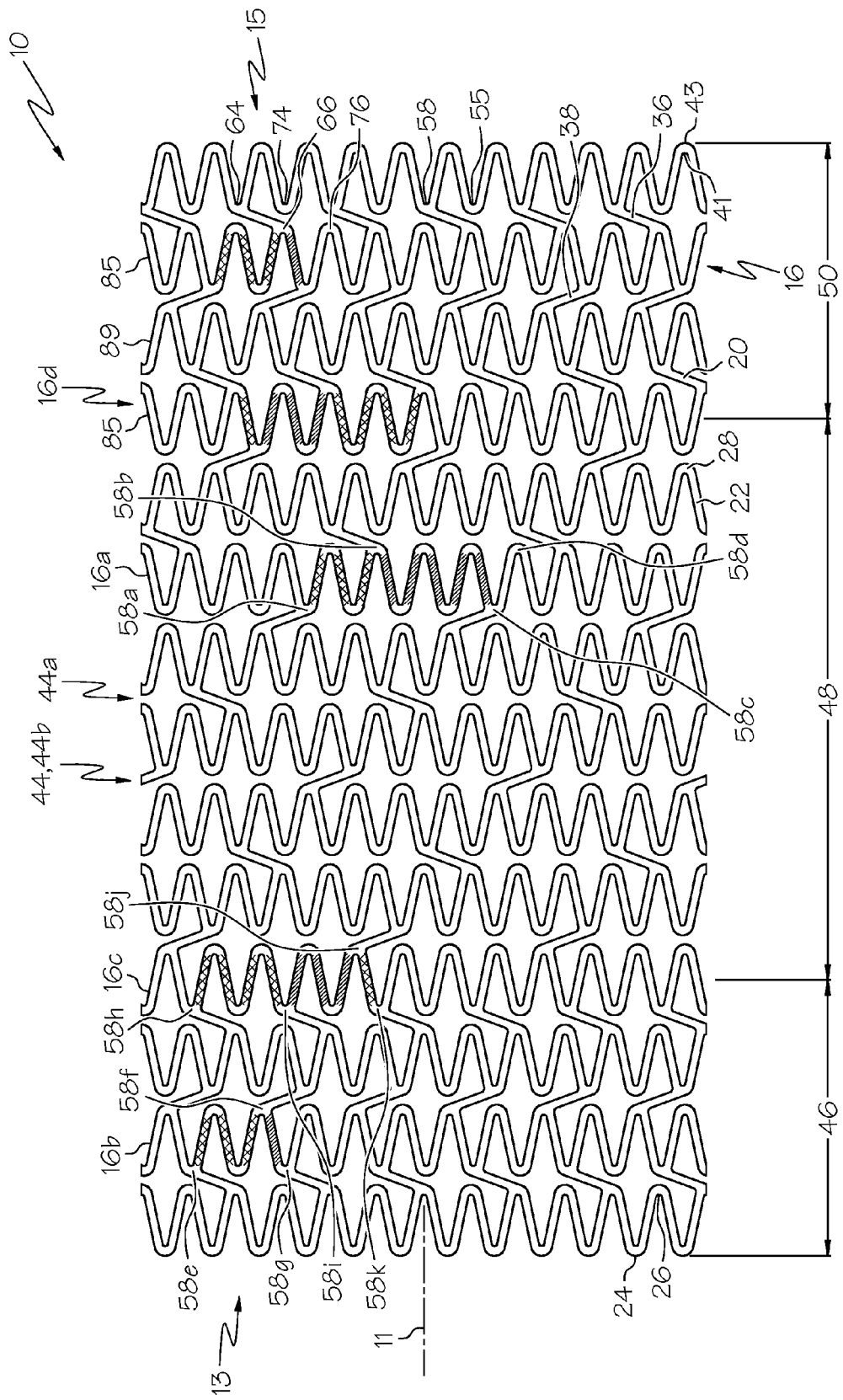
FIG. 12 shows a flat pattern for another embodiment of a stent.

FIG. 12 shows a flat pattern for another embodiment of a stent 10. The pattern of FIG. 12 has many features similar to the pattern of FIG. 11, for example as indicated by like reference characters.

In some embodiments, a stent 10 comprises a first portion 46, a second portion 48 and a third portion 50. Each portion 46, 48, 50 can comprise a portion of the length of the stent 10. In some embodiments, a connector column 44 located in the first portion 46 or the third portion 50 comprises more connector struts 20 than a connector column 44 located in the second portion 48. In some embodiments, a connector column 44 located in the first portion 46 or the third portion 50 comprises twice as many connector struts 20 as a connector column 44 located in the second portion 48. In some embodiments, each connector column 44 located in the first portion 46 or the third portion 50 comprises more connector struts 20 than each connector column 44 located in the second portion 48. In some embodiments, a connector column 44 located in the third portion 50 comprises the same number of connector struts 20 as a connector column 44 located in the first portion 46. In some embodiments, the first portion 46 and the third portion 50 can have connector columns 44 with different numbers of connectors.

In some embodiments, the third portion 50 comprises at least two connector columns 44. In some embodiments, the third portion 50 comprises at least three connector columns 44.

In some embodiments, the second portion 48 comprises more connector columns 44 than either the first portion 46 or the third portion 50. In some embodiments, the second portion 48 comprises at least twice as many connector columns 44 than either the first portion 46 or the third portion 50. In some embodiments, the second portion 48 comprises more connector columns 44 than the first portion 46 and the third portion 50 combined.

In some embodiments, the third portion 50 comprises at least one serpentine band 16 that comprises a repeating pattern of three band struts 22 and then one band strut 22 extending between connected turns 58 as the serpentine band 16 is traversed (3, 1; 3, 1; 3, 1).

In some embodiments, the third portion 50 comprises a plurality of serpentine bands 16 that have the repeating pattern of three band struts 22 and then one band strut 22 extending between adjacent connected turns 58. In some embodiments, the third portion 50 can comprise at least two or three or more of such serpentine bands 16.

A serpentine band 16 can similarly comprise a repeating pattern of two unconnected turns 55 and then zero unconnected turns 55 extending between connected turns 58 as the serpentine band 16 is traversed (2, 0; 2, 0; 2, 0).

In some embodiments, a stent 10 further comprises one or more serpentine band(s) 16 that comprise a repeating pattern of four band struts 22, then three band struts 22 and then one band strut 22 extending between connected turns 58 as the serpentine band 16 is traversed (4, 3, 1; 4, 3, 1; 4, 3, 1). For example, FIG. 12 shows one such band 16c positioned in a transition between the first region 46 and the second region 48, and another such band 16d positioned in a transition between the second region 48 and the third region 50. Further, bands 16c and 16d can have different orientations. For example, band 16c comprises a second type of band 89 with the repeating pattern extending in one circumferential direction (e.g. downward on FIG. 12), while band 16d comprises a first type of band 85 with the repeating pattern extending in a different circumferential direction (e.g. upward on FIG. 12).

A serpentine band 16c, 16d can similarly comprise a repeating pattern of three unconnected turns 55, then two unconnected turns 55 and then zero unconnected turns 55 extending between connected turns 58 as the serpentine band 16c is traversed (3, 2, 0; 3, 2, 0; 3, 2, 0).

Figure 13:
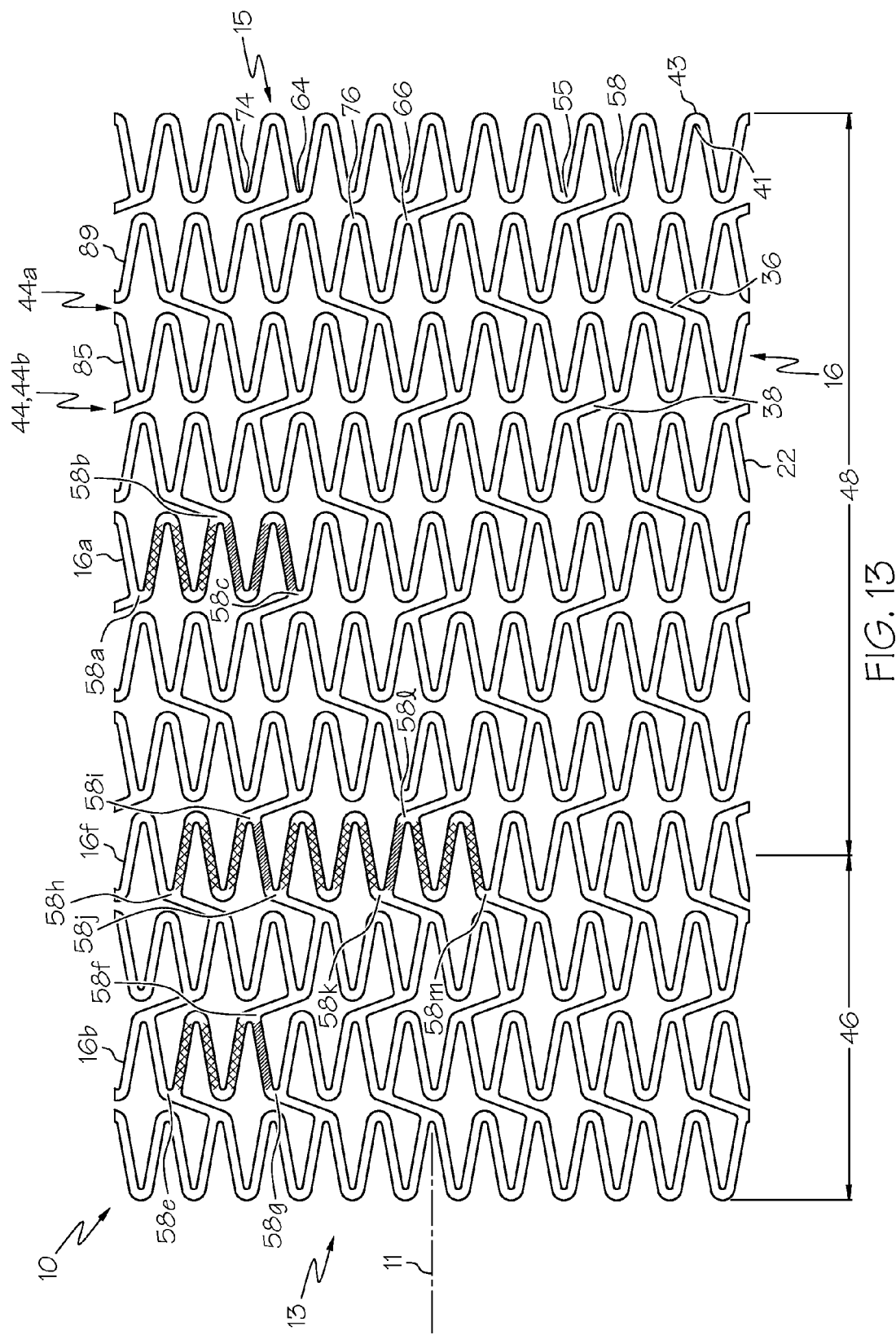
FIG. 13 shows a flat pattern for another embodiment of a stent.

FIG. 13 shows a flat pattern for another embodiment of a stent 10 having a proximal end 13, a distal end 15 and a plurality of serpentine bands 16. Adjacent serpentine bands 16 are connected across a connector column 44 by a plurality of connector struts 20.

The turns 28 of a serpentine band 16 comprise alternating proximal peaks 24 and distal valleys 26. Each turn 28 can comprise a connected turn 58 or an unconnected turn 55 depending upon whether the turn 28 connects to a connector strut 20. Similarly, proximal peaks 24 can comprise connected proximal peaks 64 or unconnected proximal peaks 74, and distal valleys 26 can comprise connected distal valleys 66 or unconnected distal valleys 76.

In some embodiments, a stent 10 comprises a first portion 46 and a second portion 48. Each portion 46, 48 can comprise a portion of the length of the stent 10. In some embodiments, a connector column 44 located in the first portion 46 comprises more connector struts 20 than a connector column 44 located in the second portion 48. In some embodiments, a connector column 44 located in the first portion 46 comprises at least 1.5 times as many connector struts 20 as a connector column 44 located in the second portion 48. In some embodiments, each connector column 44 located in the first portion 46 comprises more connector struts 20 than each connector column 44 located in the second portion 48.

In some embodiments, the first portion 46 comprises at least two connector columns 44. In some embodiments, the first portion 46 comprises at least three connector columns 44.

In some embodiments, the second portion 48 comprises more connector columns 44 than the first portion 46. In some embodiments, the second portion 48 comprises at least twice as many connector columns 44 as the first portion 46.

In some embodiments, the second portion 48 comprises at least one serpentine band 16 that comprises a repeating pattern of three band struts 22 extending between connected turns 58 as the serpentine band 16 is traversed (3; 3; 3; 3). Thus, referring to FIG. 13 and a first serpentine band 16a, starting from a first connected turn 58a, the serpentine band 16a can comprise three band struts 22 between the first connected turn 58a and a second connected turn 58b, wherein the first and second connected turns 58a, 58b can be considered "adjacent" connected turns 58 within the serpentine band 16a as the serpentine band 16a is traversed. The serpentine band 16a can further comprise three band struts 22 between the second connected turn 58b and a third connected turn 58c, and then three band struts 22 between the third connected turn 58c and the next connected turn 58, etc.

In some embodiments, the second portion 48 comprises a plurality of serpentine bands 16 that have the repeating pattern of three band struts 22 extending between adjacent connected turns 58. In some embodiments, the second portion 48 can comprise at least two, four or six or more of such serpentine bands 16a.

A serpentine band 16 can similarly comprise a repeating pattern of two unconnected turns 55 extending between connected turns 58 as the serpentine band 16 is traversed (2; 2; 2; 2). Thus, the first serpentine band 16a can comprise two unconnected turns 55 between the first connected turn 58a and the second connected turn 58b, then two unconnected turns 55 between the second connected turn 58b and the third connected turn 58c, etc.

In some embodiments, the first portion 46 comprises at least one serpentine band 16 that comprises a repeating pattern of three band struts 22 and then one band strut 22 extending between connected turns 58 as the serpentine band 16 is traversed (3, 1; 3, 1; 3, 1). Thus, a second serpentine band 16b can comprise three band struts 22 between a first connected turn 58e and a second connected turn 58f, and can further comprise one band strut 22 between the second connected turn 58f and a third connected turn 58g. The pattern can then repeat, with three band struts 22 between the third connected turn 58g and the next connected turn 58, etc.

In some embodiments, the first portion 46 comprises a plurality of serpentine bands 16 that have the repeating pattern of three band struts 22 and then one band strut 22 extending between adjacent connected turns 58. In some embodiments, the first portion 46 can comprise at least two or three or more of such serpentine bands 16.

A serpentine band 16 can similarly comprise a repeating pattern of two unconnected turns 55 and then zero unconnected turns 55 extending between connected turns 58 as the serpentine band 16 is traversed (2, 0; 2, 0; 2, 0). Thus, the second serpentine band 16b can comprise two unconnected turns 55 between the first connected turn 58e and the second connected turn 58f as the serpentine band 16b is traversed. The serpentine band 16b can further comprise zero unconnected turns 55 between the second connected turn 58f and the third connected turn 58g. The pattern can then repeat, with two unconnected turns 55 between the third connected turn 58g and the next connected turn 58, etc. This pattern can also be described as a repeating pattern of two connected turns 58 and then two unconnected turns 55 as the serpentine band 16b is traversed.

In some embodiments, a stent 10 further comprises at least one serpentine band 16 that comprises a repeating pattern of three band struts 22, then one band strut 22, then four band struts 22, then one band strut 22 and then three band struts 22 extending between connected turns 58 as the serpentine band 16 is traversed (3, 1, 4, 1, 3; 3, 1, 4, 1, 3). Thus, a third serpentine band 16f can comprise three band struts 22 between a first connected turn 58h and a second connected turn 58i, one band strut 22 between the second connected turn 58i and a third connected turn 58j, four band struts 22 between the third connected turn 58j and a fourth connected turn 58k, one band strut 22 between the fourth connected turn 58k and a fifth connected turn 58l, and three band struts 22 between the fifth connected turn 58l and a sixth connected turn 58m. The pattern can then repeat, with three band struts 22 between the sixth connected turn 58m and the next connected turn 58, etc. In some embodiments, such a serpentine band 16f can comprise a transitional band between the first portion 46 and the second portion 48 of the stent 10.

A serpentine band 16f can similarly comprise a repeating pattern of two unconnected turns 55, then zero unconnected turns 55, then three unconnected turns 55, then zero connected turns 55 and then two unconnected turns 55 extending between connected turns 58 as the serpentine band 16f is traversed (2, 0, 3, 0, 2; 2, 0, 3, 0, 2). Thus, the third serpentine band 16f can comprise two unconnected turns 55 between the first connected turn 58h and the second connected turn 58i as the serpentine band 16f is traversed. The serpentine band 16f can further comprise zero unconnected turns 55 between the second connected turn 58i and the third connected turn 58j, three unconnected turns 55 between the third connected turn 58j and the fourth connected turn 58k, zero unconnected turns 55 between the fourth connected turn 58k and the fifth connected turn 58l, and two unconnected turns 55 between the fifth connected turn 58l and the sixth connected turn 58m. The pattern can then repeat, with two unconnected turns 55 between the sixth connected turn 58m and the next connected turn 58, etc. This pattern can also be described as a repeating pattern of two unconnected turns 55, two connected turns 58, three unconnected turns 55, two connected turns 58, two unconnected turns 55 and then one connected turn 58 as the serpentine band 16f is traversed.

Serpentine bands 16 can comprise a first type of serpentine band 85 and a second type of serpentine band 89. In some embodiments, each first type of serpentine band 85 is aligned with one another such that similar portions of each band 85 align along the length of the stent 10. For example, a proximal peak 24 of a first type of serpentine band 85 can be aligned with a proximal peak 24 of another first type of serpentine band 85 in a direction parallel to the stent longitudinal axis 11. Each second type of serpentine band 89 is aligned with one another such that similar portions of each band 89 align along the length of the stent 10. For example, a proximal peak 24 of a second type of serpentine band 89 can be aligned with a proximal peak 24 of another second type of serpentine band 89 in a direction parallel to the stent longitudinal axis 11. Each first type of serpentine band 85 can be offset from each second type of serpentine band 89 such that similar portions of the different types of bands 85, 89 are not aligned along the length of the stent. A proximal peak 24 of a first type of serpentine band 85 can further be aligned with a distal valley 26 of a second type of serpentine band 89 in a direction parallel to the stent longitudinal axis 11.

In some embodiments, the first type of serpentine band 85 and the second type of serpentine band 89 can alternate along the length of the stent 10.

Figure 14:
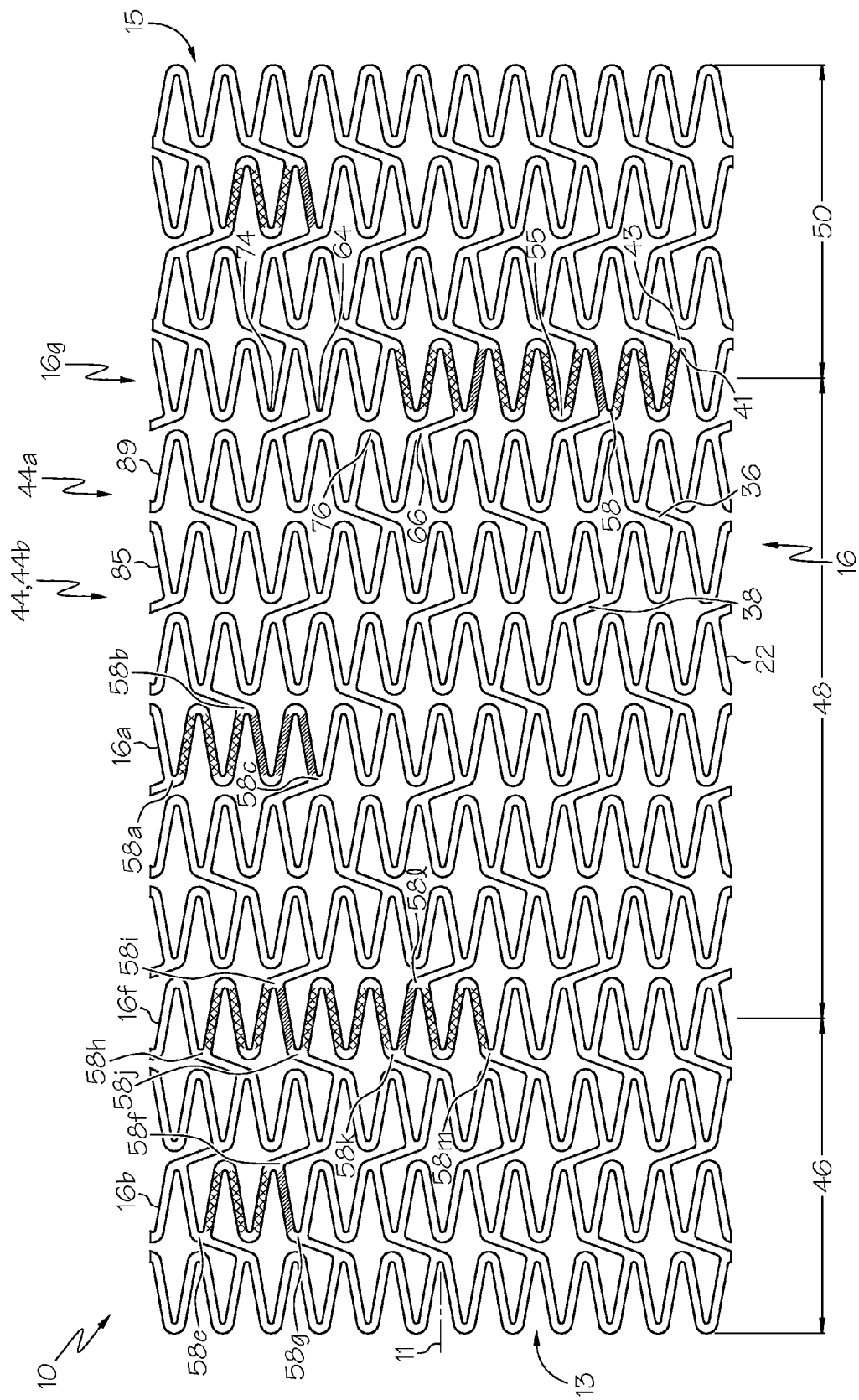
FIG. 14 shows a flat pattern for another embodiment of a stent.

FIG. 14 shows a flat pattern for another embodiment of a stent 10. The pattern of FIG. 14 has many features similar to the pattern of FIG. 13, for example as indicated by like reference characters.

In some embodiments, a stent 10 comprises a first portion 46, a second portion 48 and a third portion 50. Each portion 46, 48, 50 can comprise a portion of the length of the stent 10. In some embodiments, a connector column 44 located in the first portion 46 or the third portion 50 comprises more connector struts 20 than a connector column 44 located in the second portion 48. In some embodiments, a connector column 44 located in the first portion 46 or the third portion 50 comprises twice as many connector struts 20 as a connector column 44 located in the second portion 48. In some embodiments, each connector column 44 located in the first portion 46 or the third portion 50 comprises more connector struts 20 than each connector column 44 located in the second portion 48. In some embodiments, a connector column 44 located in the third portion 50 comprises the same number of connector struts 20 as a connector column 44 located in the first portion 46. In some embodiments, the first portion 46 and the third portion 50 can have connector columns 44 with different numbers of connectors.

In some embodiments, the third portion 50 comprises at least two connector columns 44. In some embodiments, the third portion 50 comprises at least three connector columns 44.

In some embodiments, the second portion 48 comprises more connector columns 44 than either the first portion 46 or the third portion 50. In some embodiments, the second portion 48 comprises at least twice as many connector columns 44 than either the first portion 46 or the third portion 50. In some embodiments, the second portion 48 comprises more connector columns 44 than the first portion 46 and the third portion 50 combined.

In some embodiments, the third portion 50 comprises at least one serpentine band 16 that comprises a repeating pattern of three band struts 22 and then one band strut 22 extending between connected turns 58 as the serpentine band 16 is traversed (3, 1; 3, 1; 3, 1).

In some embodiments, the third portion 50 comprises a plurality of serpentine bands 16 that have the repeating pattern of three band struts 22 and then one band strut 22 extending between adjacent connected turns 58. In some embodiments, the third portion 50 can comprise at least two or three or more of such serpentine bands 16.

A serpentine band 16 can similarly comprise a repeating pattern of two unconnected turns 55 and then zero unconnected turns 55 extending between connected turns 58 as the serpentine band 16 is traversed (2, 0; 2, 0; 2, 0).

In some embodiments, a stent 10 further comprises one or more serpentine band(s) 16 that comprise a repeating pattern of three band struts 22, then one band strut 22, then four band struts 22, then one band strut 22 and then three band struts 22 extending between connected turns 58 as the serpentine band 16 is traversed (3, 1, 4, 1, 3; 3, 1, 4, 1, 3). For example, FIG. 14 shows one such band 16f positioned in a transition between the first region 46 and the second region 48, and another such band 16g positioned in a transition between the second region 48 and the third region 50. Further, bands 16f and 16g can have different orientations. For example, band 16f comprises a second type of band 89, while band 16g comprises a first type of band 85.

A serpentine band 16f, 16g can similarly comprise a repeating pattern of two unconnected turns 55, then zero unconnected turns 55, then three unconnected turns 55, then zero connected turns 55 and then two unconnected turns 55 extending between connected turns 58 as the serpentine band 16f, 16g is traversed (2, 0, 3, 0, 2; 2, 0, 3, 0, 2).

The inventive stents may be made from any suitable biocompatible materials including one or more polymers, one or more metals or combinations of polymer(s) and metal(s). Examples of suitable materials include biodegradable materials that are also biocompatible. In some embodiments, a stent can have one or more components constructed from one or more metals, polymers or combinations thereof that are corrodible so as to dissolve, dissociate or otherwise break down in the body without ill effect. Examples of such materials have been referred to as being degradable, biodegradable, biologically degradable, erodable, bioabsorbable, bioresorbable, and the like. Biodegradable material will generally undergo breakdown or decomposition into harmless compounds as part of a normal biological process. Suitable biodegradable materials include polylactic acid, polyglycolic acid (PGA), collagen or other connective proteins or natural materials, polycaprolactone, hylauric acid, adhesive proteins, co-polymers of these materials as well as composites and combinations thereof and combinations of other biodegradable polymers. Other polymers that may be used include polyester and polycarbonate copolymers. Examples of suitable metals include, but are not limited to, stainless steel, titanium, tantalum, platinum, tungsten, gold and alloys of any of the above-mentioned metals. Examples of suitable alloys include platinum-iridium alloys, cobalt-chromium alloys including Elgiloy and Phynox, MP35N alloy and nickel-titanium alloys, for example, Nitinol. Some further examples of biodegradable alloys, such as magnesium alloys and zinc alloys, are disclosed in U.S. Pat. No. 6,854,172 and US 2006/0052864, the entire contents of which are hereby incorporated herein by reference.

The inventive stents may be made of shape memory materials such as superelastic Nitinol or spring steel, or may be made of materials which are plastically deformable. In the case of shape memory materials, the stent may be provided with a memorized shape and then deformed to a reduced diameter shape. The stent may restore itself to its memorized shape upon being heated to a transition temperature and having any restraints removed therefrom.

The inventive stents may be created by methods including cutting or etching a design from a tubular stock, from a flat sheet which is cut or etched and which is subsequently rolled or from one or more interwoven wires or braids. Any other suitable technique which is known in the art or which is subsequently developed may also be used to manufacture the inventive stents disclosed herein.

In some embodiments the stent, the delivery system or other portion of the assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

In some embodiments the at least a portion of the stent is configured to include one or more mechanisms for the delivery of a therapeutic agent. Often the agent will be in the form of a coating or other layer (or layers) of material placed on a surface region of the stent, which is adapted to be released at the site of the stent's implantation or areas adjacent thereto.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Some other examples of therapeutic agents include everolimus and sirolimus, their analogs and conjugates. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below. This completes the description of the invention. Those skilled in the art may recognize other equivalents to the specific embodiment described herein which equivalents are intended to be encompassed by the claims attached hereto.

What is claimed is as follows:

1. A stent comprising a plurality of serpentine bands and a plurality of connector columns, each serpentine band comprising a plurality of alternating straight band struts and turns, adjacent serpentine bands connected across a connector column by a plurality of connector struts, each connector strut connected at one end to a turn of one serpentine band and connected at the other end to a turn of another serpentine band, the turns of a serpentine band comprising connected turns that connect to a connector strut and unconnected turns that do not connect to a connector strut;
    at least one serpentine band comprising a repeating pattern of three band struts, then a connected turn, then five band struts and then a next connected turn as the serpentine band is traversed;
    at least one serpentine band comprising a repeating pattern of three band struts, then a connected turn, then one band strut and then a next connected turn, as the serpentine band is traversed; and
    at least one serpentine band comprises a repeating pattern of four band struts, then a connected turn, then three band struts, then a next connected turn, then one band strut and then a next connected turn as the serpentine band is traversed.

2. The stent of claim 1, wherein a plurality of the serpentine bands each comprise a repeating pattern of four band struts, then a connected turn, then three band struts then a next connected turn, then one band strut and then a next connected turn as the serpentine band is traversed.

3. The stent of claim 1, wherein a plurality of the serpentine bands comprise a repeating pattern of three band struts, then a connected turn, then five band struts and then a next connected turn.

4. The stent of claim 1, wherein a plurality of the serpentine bands comprise a repeating pattern of three band struts, then a connected turn, then one band strut and then a next connected turn.

5. The stent of claim 1, comprising a first length portion and a second length portion, wherein a connector column in the first length portion comprises more connector struts than a connector column in the second length portion.

6. The stent of claim 5, wherein each connector column in the first length portion comprises more connector struts than each connector column in the second length portion.

7. The stent of claim 6, wherein the first length portion comprises at least two connector columns.

8. The stent of claim 1, wherein the connector columns comprise first connector columns and second connector columns, connector struts of the first connector columns being parallel to one another, connector struts of the second connector columns being nonparallel to the connector struts of the first connector columns.

9. The stent of claim 8, wherein first connector columns and second connector columns alternate along the length of the stent.

10. The stent of claim 1, wherein the turns of each serpentine band comprise alternating proximal peaks and distal valleys, the proximal peaks of one serpentine band aligned in a stent axial direction with the distal valleys of an adjacent serpentine band.

11. A stent comprising a plurality of serpentine bands and a plurality of connector columns, each serpentine band comprising a plurality of alternating straight band struts and turns, adjacent serpentine bands connected across a connector column by a plurality of connector struts, each connector strut connected at one end to a turn of one serpentine band and connected at the other end to a turn of another serpentine band, the turns of a serpentine band comprising connected turns that connect to a connector strut and unconnected turns that do not connect to a connector strut;

at least three serpentine bands each comprising a repeating pattern of three band struts, then a connected turn, then five band struts and then a next connected turn as the serpentine band is traversed;

at least one serpentine band comprising a repeating pattern of three band struts, then a connected turn, then one band strut and then a next connected turn as the serpentine band is traversed; and at least serpentine band comprises a repeating pattern of four band struts, then a connected turn, then three band struts, then a next connected turn, and then one band strut and then a next connected turn as the serpentine band is traversed.

12. The stent of claim 11, wherein a plurality of the serpentine bands each comprise a repeating pattern of four band struts, then a connected turn, then three band struts, then a next connected turn, then one band strut and then a next connected turn, as the serpentine band is traversed.

13. The stent of claim 12, wherein the serpentine bands that each comprise the repeating pattern of three band struts, then a connected turn, then five band struts and then a next connected turn are located between the serpentine bands that each comprise the repeating pattern of four band struts, then a connected turn, then three band struts, then a next connected turn, then one band strut and then a next connected turn.

14. The stent of claim 11, wherein a plurality of the serpentine bands each comprise a repeating pattern of three band struts, then a connected turn, then one band strut and then a next connected turn.

15. The stent of claim 11, wherein at least three of the serpentine bands each comprise a repeating pattern of three band struts, then a connected turn, then one band strut and then a next connected turn.

16. The stent of claim 11, comprising a first length portion and a second length portion, wherein a connector column in the first length portion comprises more connector struts than a connector column in the second length portion.

17. The stent of claim 16, wherein each connector column in the first length portion comprises more connector struts than each connector column in the second length portion.

18. The stent of claim 16, further comprising a third length portion, the second length portion located between the first length portion and the third length portion, wherein a connector column in the third length portion comprises more connector struts than a connector column in the second length portion.

19. The stent of claim 16, wherein a connector column in the second length portion has half as many connector struts as a connector column in the first length portion.

* * * * *